(12) United States Patent
Yoshida et al.

(10) Patent No.: US 10,067,145 B2
(45) Date of Patent: *Sep. 4, 2018

(54) METHOD FOR REMOVING GENOMICALLY UNSTABLE IPS CELLS AND SYNTHETIC PEPTIDE USED THEREFOR

(71) Applicants: TOAGOSEI CO., LTD., Tokyo (JP); KYOTO UNIVERSITY, Kyoto-shi, Kyoto (JP)

(72) Inventors: Tetsuhiko Yoshida, Tsukuba (JP); Nahoko Baileykobayashi, Tsukuba (JP); Yoshinori Yoshida, Kyoto (JP); Kazuhisa Chonabayashi, Kyoto (JP)

(73) Assignees: TOAGOSEI CO., LTD., Tokyo (JP); KYOTO UNIVERSITY, Kyoto-shi (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/033,452

(22) PCT Filed: Oct. 30, 2014

(86) PCT No.: PCT/JP2014/078964
§ 371 (c)(1),
(2) Date: Apr. 29, 2016

(87) PCT Pub. No.: WO2015/064715
PCT Pub. Date: May 7, 2015

(65) Prior Publication Data
US 2016/0252523 A1 Sep. 1, 2016

(30) Foreign Application Priority Data
Oct. 30, 2013 (JP) ................. 2013-225922

(51) Int. Cl.
| | | |
|---|---|---|
| G01N 33/68 | (2006.01) | |
| C07K 7/06 | (2006.01) | |
| C07K 7/08 | (2006.01) | |
| C07K 14/47 | (2006.01) | |
| C12Q 1/6876 | (2018.01) | |
| G01N 15/14 | (2006.01) | |
| G01N 15/00 | (2006.01) | |
| G01N 15/10 | (2006.01) | |

(52) U.S. Cl.
CPC ........ *G01N 33/6872* (2013.01); *C07K 7/06* (2013.01); *C07K 7/08* (2013.01); *C07K 14/4705* (2013.01); *C07K 14/4725* (2013.01); *C12Q 1/6876* (2013.01); *G01N 15/14* (2013.01); *G01N 15/1463* (2013.01); *C07K 2319/01* (2013.01); *C12Q 2600/158* (2013.01); *G01N 2015/0065* (2013.01); *G01N 2015/1006* (2013.01); *G01N 2015/149* (2013.01); *G01N 2015/1488* (2013.01); *G01N 2333/4703* (2013.01); *G01N 2333/4706* (2013.01)

(58) Field of Classification Search
None
See application file for complete search history.

(56) References Cited

U.S. PATENT DOCUMENTS

| | | | |
|---|---|---|---|
| 2004/0214272 A1* | 10/2004 | La Rosa | C07H 21/04 435/69.1 |
| 2006/0068386 A1* | 3/2006 | Slesarev | C07K 14/195 435/6.18 |
| 2010/0297758 A1 | 11/2010 | Yoshida et al. | |
| 2014/0220681 A1* | 8/2014 | Valamehr | C12N 5/0696 435/366 |

FOREIGN PATENT DOCUMENTS

| | | |
|---|---|---|
| JP | 2012-223104 A | 11/2012 |
| WO | 2008-028965 A2 | 3/2008 |
| WO | 2009/093692 A1 | 7/2009 |
| WO | 2012-087965 A2 | 6/2012 |

OTHER PUBLICATIONS

Boileve et al., Cell Cycle 12:3, 473-479; Feb. 1, 2013.*
Tapia et al., J Exp Med. Sep. 27, 2010;207(10):2045-2048.*
Kepp et al., "Viral subversion of immunogenic cell death", Cell Cycle, 2009, vol. 8, Issue 6, pp. 860-869.
Obeid et al., "Leveraging the Immune System during Chemotherapy: Moving Calreticulin to the Cell Surface Converts Apoptotic Death from "Silent"To Immunogenic", Cancer Research, 2007, vol. 67, No. 17, pp. 7941-7944.
Salisbury et al., "Centrin-2 Is Required for Centriole Duplication in Mammalian Cells", Current Biology, 2002, vol. 12, pp. 1287-1292.
Senovilla et al., "An Immunosurveillance Mechanism Controls Cancer Cell Ploidy" Science, 2012, vol. 337, pp. 1678-1684.

* cited by examiner

Primary Examiner — Daniel C Gamett
(74) Attorney, Agent, or Firm — Oliff PLC

(57) ABSTRACT

The present invention provides a method that allows highly efficient and highly reliable evaluation of genomic stability of pluripotent stem cells, a method for removing pluripotent stem cells that have been identified as genomically unstable by the evaluation method from a culture of pluripotent stem cells to be evaluated, and a synthetic peptide that can be used for the methods. The methods provided by the present invention include preparing a culture of pluripotent stem cells of interest and analyzing an expression level of calreticulin for the pluripotent stem cells in the culture followed by identifying genomic stability or genomic instability of the stem cells on the basis of the expression level of calreticulin.

17 Claims, 8 Drawing Sheets

Specification includes a Sequence Listing.

[Fig. 1]
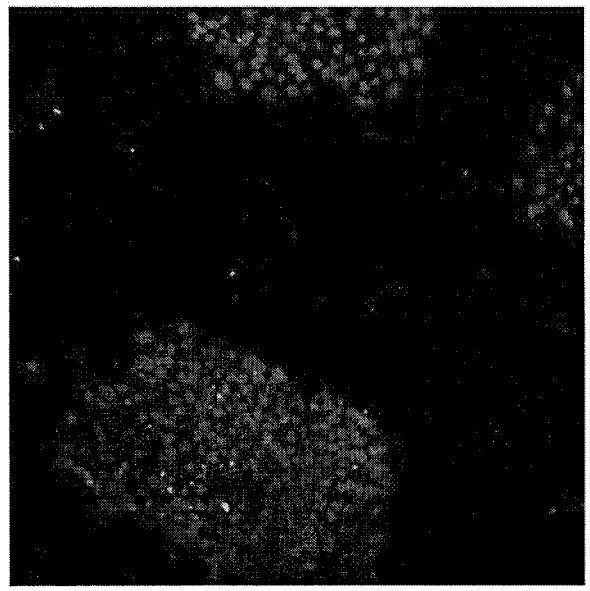

[Fig. 2]
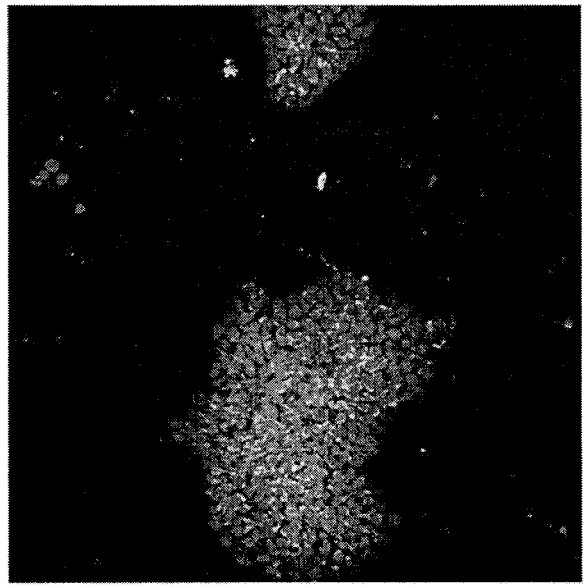

[Fig. 3]
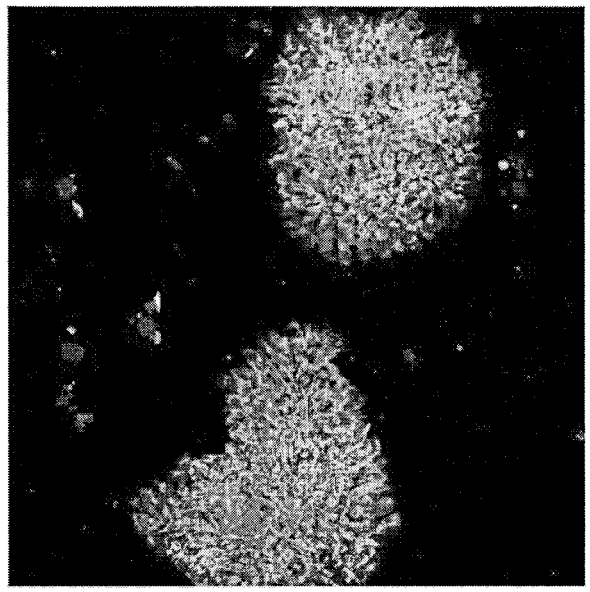

[Fig. 4]
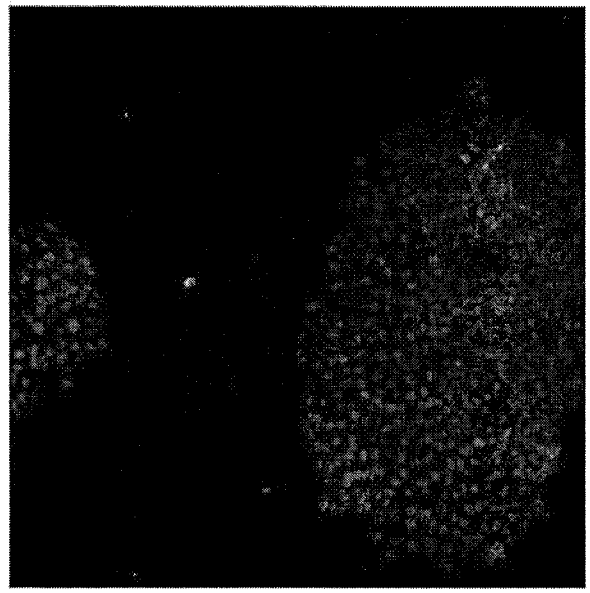

[Fig. 5]
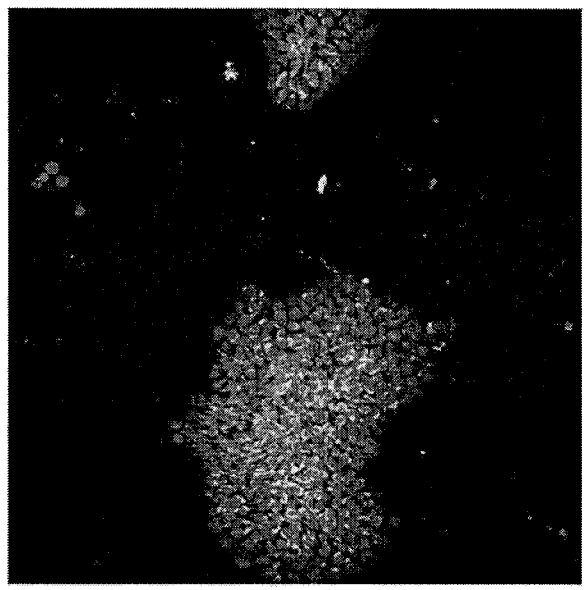

[Fig. 6]
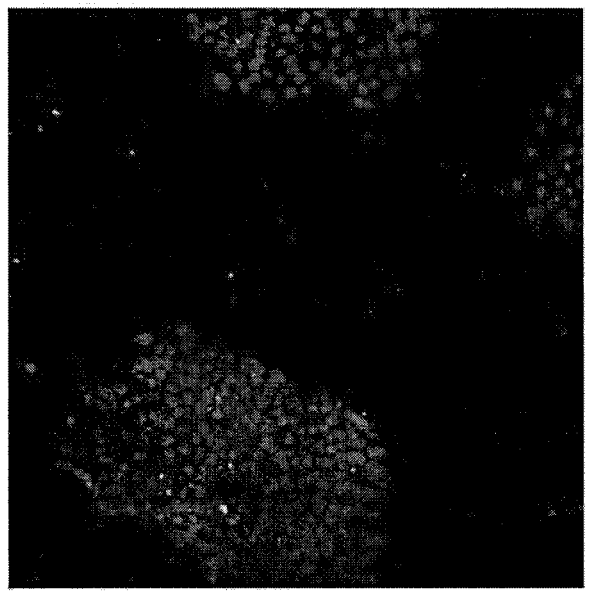

[Fig. 7]
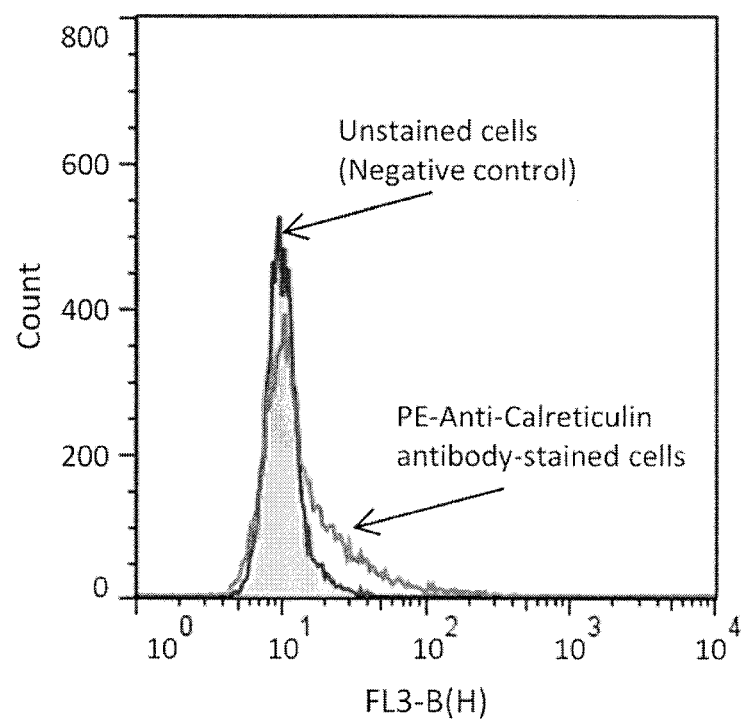

[Fig. 8]
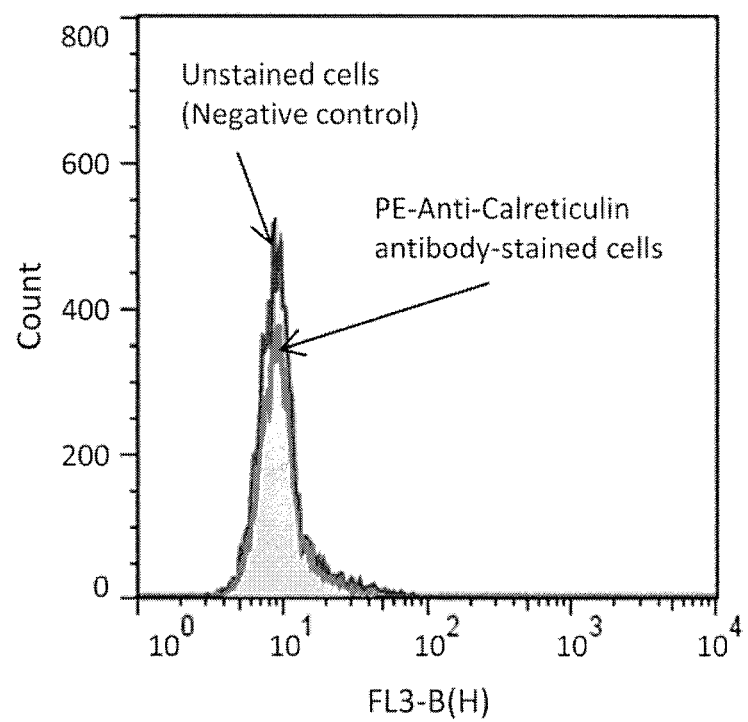

US 10,067,145 B2

METHOD FOR REMOVING GENOMICALLY UNSTABLE IPS CELLS AND SYNTHETIC PEPTIDE USED THEREFOR

TECHNICAL FIELD

The present invention relates to a method for evaluating genomic stability of pluripotent stem cells such as embryonic stem cells (hereinafter also referred to as "ES cells") and induced pluripotent stem cells (hereinafter also referred to as "iPS cells") and to a synthetic peptide used for the method. The present invention also relates to a method for removing genomically unstable pluripotent stem cells from a culture containing pluripotent stem cells.

The present invention claims the priority to Japanese Patent Application No. 2013-225922 filed on 30 Oct. 2013, which is incorporated herein by reference in its entirety.

BACKGROUND ART

One of the challenges upon application of pluripotent stem cells (typically iPS cells and ES cells) derived from humans or a mammal other than humans for regenerative therapy (typically transplantation therapy) is establishment of the technique that allows highly efficient production of the stem cells applicable to the therapy.

For example, pluripotent stem cells such as genomically unstable iPS cells are not suitable for in vivo transplantation, and thus genomically unstable pluripotent stem cells are required to be removed from a population of pluripotent stem cells of interest to obtain pluripotent stem cells such as iPS cells applicable to regenerative therapy. Upon removal of genomically unstable pluripotent stem cells, it is naturally required to evaluate the genomic stability of pluripotent stem cells.

However, methods for evaluation of genomic stability of pluripotent stem cells which have been reported so far (e.g. chromosome banding and fluorescence in situ hybridization (FISH)) require complicated procedures or proficient skills. Therefore, there is a need for a method that allows simple and highly efficient evaluation of genomic stability of pluripotent stem cells. Further, because many conventional evaluation methods require fixation of target cells, it has been difficult to directly evaluate genomic stability of pluripotent stem cells per se which are actually used for regenerative therapy (i.e. living cells).

CITATION LIST

Patent Literature

[Patent Literature 1] WO 2009/093692

Non Patent Literature

[Non Patent Literature 1] Cell Cycle, Vol. 8 (No. 6), 2009, pp. 860-869
[Non Patent Literature 2] Cancer Research, Vol. 67 (No. 17), 2007, pp. 7941-7944
[Non Patent Literature 3] Current Biology, Vol. 12, 2002, pp. 1287-1292

SUMMARY OF INVENTION

Thus, the present invention, which is to solve the conventional problems involved in application of pluripotent stem cells, provides a method that allows highly efficient and highly reliable evaluation of genomic stability of pluripotent stem cells. The present invention also provides a method for removing pluripotent stem cells that have been identified as genomically unstable by the evaluation method from a culture of pluripotent stem cells of interest. Another object of the present invention is to provide a peptide which is a relatively short-chain, artificially synthesised peptide and can be used for improving effects of the evaluation method and the removal method. Another object of the present invention is to provide a composition including the peptide.

The inventor of the present invention focused on calreticulin protein (hereinafter also referred to as "calreticulin"), a known immunostimulating protein (so-called eat-me signal) which is known to be localised inside of normal cells (typically in endoplasmic reticulum) while expression of which at the cell surface is induced upon immunogenic apoptosis in cancer cells and cells infected with pathogens (Non Patent Literature 1 and Non Patent Literature 2).

The inventor analyzed the expression level of calreticulin in various pluripotent stem cells and surprisingly found that the expression level of calreticulin in genomically unstable pluripotent stem cells (e.g. iPS cells) is significantly increased compared to genomically stable stem cells of the same type. Thus, the inventor has completed the present invention.

In order to achieve the above objects, the present invention provides a method for evaluating genomic stability of pluripotent stem cells of interest (genomic stability evaluation method) including preparing a culture of pluripotent stem cells such as iPS cells derived from humans or a mammal other than humans and analyzing the expression level of calreticulin for the pluripotent stem cells in the culture (the abundance of calreticulin expressed on the surface of the pluripotent stem cells (typically on the surface of cell membrane)) followed by identifying genomic stability or instability of the pluripotent stem cells on the basis of the expression level of calreticulin. The pluripotent stem cell genomic stability evaluation method described herein is characterized in that pluripotent stem cells, for which the expression level of calreticulin of the stem cells is above a prescribed level, are identified as genomically unstable.

By using the pluripotent stem cell genomic stability evaluation method described herein, genomic stability or genomic instability of stem cells can be identified by such a simple procedure as analyzing the expression level of calreticulin for pluripotent stem cells in a pluripotent stem cell culture (typically in an iPS cell culture or an ES cell culture). Accordingly, genomic stability of pluripotent stem cells such as iPS cells can be easily evaluated with high efficiency. The genomic stability evaluation method can be particularly suitably used for evaluation of genomic stability of a high amount of pluripotent stem cells (e.g. establishment of iPS cell clones and preparation of iPS cells for regenerative therapy).

A preferable embodiment of the pluripotent stem cell genomic stability evaluation method described herein is characterized in that the identification of genomic stability or instability of the pluripotent stem cells on the basis of the expression level of calreticulin is carried out by an immunological assay using an antibody specifically reacting with calreticulin or a fragment thereof (i.e. an anti-calreticulin antibody).

According to an immunological assay using an anti-calreticulin antibody, expression of calreticulin in pluripotent stem cells in a pluripotent stem cell culture (typically in an iPS cell culture or an ES cell culture) of interest can be specifically examined with high sensitivity. Thus genomic stability or genomic instability of pluripotent stem cells such as iPS cells can be identified with high accuracy and high reliability. Evaluation of genomic stability of pluripotent stem cells using an immunological assay is also preferable because genomic stability of pluripotent stem cells such as iPS cells can be evaluated in a shorter time and with a simpler manner than conventional methods for evaluating genomic stability (e.g. FISH).

The inventor of the present invention also searched for a substance that increases particularly the expression level of calreticulin in genomically unstable pluripotent stem cells (typically iPS cells or ES cells) in order to increase the effect of the method for evaluating genomic stability of pluripotent stem cells. As a result of extensive studies, the inventor designed amino acid sequences translated from an RNA sequence included in siRNA (small interfering RNA) of human centrin 2 (centrosome-related protein), and found that synthetic peptides prepared to include the amino acid sequences have an ability (calreticulin expression inducing activity) to increase the expression level of calreticulin or induce expression of calreticulin in genomically unstable pluripotent stem cells (typically iPS cells) when the synthetic peptides are supplied to pluripotent stein cells (typically to a medium of a culture of pluripotent stem cells such as iPS cells) of interest.

On the basis of the above finding, the inventor of the present invention has completed, as another aspect of the present invention, an artificially synthesised peptide (hereinafter referred to as "calreticulin expression inducing peptide") that exhibits calreticulin expression inducing activity on genomically unstable pluripotent stem cells (typically iPS cells or ES cells).

Specifically, the present invention provides a synthetic peptide comprising a calreticulin expression inducing peptide sequence consisting of either of the following amino acid sequences:

```
                                       (SEQ ID NO: 1)
CRAKAGDPC;
and (SEQ ID NO: 2)
CEQKQEIRC;
``` or a modified amino acid sequence formed by substitution, deletion and/or addition of 1 or a few (typically 2 or 3) amino acid residues in/from/to the above amino acid sequences.

The synthetic peptide described herein can be readily and artificially produced by chemical synthesis (or biosynthesis). In addition, the peptide per se has a simple structure (linear peptide chain), and thus is easily handled. By such a simple process as, for example, adding the calreticulin expression inducing peptide to pluripotent stem cells such as iPS cells (typically into a medium of a culture of the stem cells), the expression level of calreticulin of genomically unstable pluripotent stem cells (typically iPS cells) can be increased.

According to the present invention, as a preferable embodiment of the pluripotent stem cell genomic stability evaluation method described herein, an evaluation method is provided that is characterized in that the method includes, prior to identification of genomic stability or instability of the pluripotent stem cells based on the expression level of calreticulin as described above, supplying, at least once, to a pluripotent stem cell culture of interest at least one calreticulin expression inducing peptide described herein and carrying out the identification after culturing, for a prescribed time, the pluripotent stem cell culture to which the synthetic peptide has been supplied at least once.

By using the calreticulin expression inducing peptide to increase the expression level of calreticulin in genomically unstable pluripotent stem cells (typically iPS cells or ES cells), it is possible to obtain an unambiguous difference in the expression level of calreticulin between genomically unstable pluripotent stem cells and genomically stable pluripotent stem cells. This makes the discrimination between genomic stability and genomic instability of pluripotent stem cells such as iPS cells based on expression of calreticulin easy, and thus the accuracy and reliability of the pluripotent stem cell genomic stability evaluation method can be increased.

In a preferable embodiment of the calreticulin expression inducing peptide described herein, the modified amino acid sequence is an amino acid sequence of SEQ ID NO: 1 or 2 from which N-terminal and C-terminal cysteine residues (C) are deleted.

The calreticulin expression inducing peptide sequence consisting of the modified amino acid sequence can also exhibit preferable calreticulin expression inducing activity as the calreticulin expression inducing peptide sequence represented by SEQ ID NO: 1 or 2.

A preferable embodiment of the calreticulin expression inducing peptide described herein comprises a membrane-penetrating peptide sequence N-terminal or C-terminal to the calreticulin expression inducing peptide sequence.

The calreticulin expression inducing peptide comprising the membrane-penetrating peptide allows transfer of the calreticulin expression inducing peptide sequence with high efficiency into pluripotent stem cells such as iPS cells (inside of cell membrane and/or nuclear membrane), and thus can be suitably used for the present invention.

A preferable embodiment of the calreticulin expression inducing peptide described herein comprises the membrane-penetrating peptide sequence consisting of the following amino acid sequence:

```
                                       (SEQ ID NO: 5)
KKRTLRKNDRKKR.
```

The amino acid sequence described herein under SEQ ID NO: 5 is a typical example of the amino acid sequence included in membrane-penetrating peptides and can efficiently induce calreticulin expression particularly in genomically unstable pluripotent stem cells (typically iPS cells).

In a preferable embodiment of the calreticulin expression inducing peptide described herein, the synthetic peptide has 30 or less amino acid residues in total.

The peptide having such a short peptide chain is easily obtained by chemical synthesis, is inexpensive and is easily handled, and thus is particularly suitably used for the present invention.

A preferable embodiment of the calreticulin expression inducing peptide described herein comprises any of the following amino acid sequences:

```
                                       (SEQ ID NO: 10)
         KKRTLRKNDRKKRGGCRAKAGDPC;

(SEQ ID NO: 11)
         KKRTLRKNDRKKRGGCEQKQEIRC;

(SEQ ID NO: 12)
         KKRTLRKNDRKKRGGRAKAGDP;
         and
```

-continued

KKRTLRKNDRKKRGGEQKQEIR. (SEQ ID NO: 13)

The synthetic peptide exhibits calreticulin expression inducing activity particularly on genomically unstable iPS cells derived from humans. The synthetic peptide suitably applied to human iPS cells is highly valuable for applications in the medical industry.

Another aspect of the present invention provides a method for removing genomically unstable pluripotent stem cells from a culture of interest containing pluripotent stem cells derived from humans or a mammal other than humans, comprising identifying genomic stability or an extent thereof of pluripotent stem cells in the pluripotent stem cell culture of interest according to the pluripotent stem cell genomic stability evaluation method described herein and removing pluripotent stem cells that have been identified as genomically unstable by the identification method from the pluripotent stem cell culture.

By removing the pluripotent stem cells that have been identified as genomically unstable from a pluripotent stem cell culture (typically from an iPS cell culture or an ES cell culture) of interest, a pluripotent stem cell culture (e.g. an iPS cell culture) mainly containing pluripotent stem cells that have been identified as genomically stable (preferably consisting of pluripotent stem cells that have been identified as genomically stable) can be prepared. Thus, the removal method of genomically unstable pluripotent stem cells can be suitably used for preparation of a culture of pluripotent stem cells such as iPS cells that can be used for regenerative therapy. In addition, by identifying genomic stability or instability of pluripotent stem cells of interest by the pluripotent stem cell genomic stability evaluation method, genomically unstable pluripotent stem cells (preferably iPS cells) can be removed with high efficiency and high accuracy.

A preferable embodiment of the method for removing genomically unstable pluripotent stem cells described herein is characterized in that the pluripotent stem cells that have been identified as genomically unstable are removed by using a cell sorter.

By using a cell sorter, the pluripotent stem cells that have been identified as genomically unstable can be efficiently removed from the culture containing pluripotent stem cells (typically iPS cells or ES cells). The removal method of genomically unstable pluripotent stem cells using a cell sorter is thus particularly suitable for removal of cells from a culture containing a high amount of pluripotent stem cells (typically iPS cells).

Typically, the pluripotent stem cells which are removed by the method for removing genomically unstable pluripotent stem cells are pluripotent stem cells having a chromosome aberration. Pluripotent stem cells such as iPS cells (or cells, a cell cluster, a tissue and the like obtained by induction of differentiation of the stem cells) having a chromosome aberration may cause tumours after in vivo transplantation, and thus the method for removing pluripotent stem cells having a chromosome aberration can be suitably used as a method for preparing pluripotent stem cells (typically iPS cells) for regenerative therapy. The removal method wherein the cells to be removed are human iPS cells having a chromosome aberration is a particularly preferable embodiment of the present invention.

Another aspect of the present invention provides a method for producing a culture containing pluripotent stem cells derived from humans or a mammal other than humans, comprising removing, during cultivation of the pluripotent stem cells, genomically unstable pluripotent stem cells from the pluripotent stem cell culture by the removal method of genomically unstable pluripotent stem cells described herein.

The pluripotent stem cell culture (typically iPS cell culture or ES cell culture) produced by the method is a pluripotent stem cell culture from which genomically unstable pluripotent stem cells are removed by the removal method, and thus may be understood to be a pluripotent stem cell culture in which substantially all pluripotent stem cells in the culture are genomically stable. The pluripotent stem cell culture (typically pluripotent stem cells in the pluripotent stem cell culture) can be suitably used as pluripotent stem cells for regenerative therapy having low risk of neoplastic transformation. The method for producing a culture particularly containing human iPS cells is highly valuable for applications in the medical industry, and thus is a preferable embodiment.

Another aspect of the present invention provides an agent for inducing calreticulin expression used for increasing the expression level of calreticulin of genomically unstable pluripotent stem cells, comprising at least one calreticulin expression inducing peptide described herein.

Typically, the agent for inducing calreticulin expression comprises at least one pharmaceutically acceptable carrier (such as at least one substrate contributing to an improvement in stability of the peptide or a liquid medium including saline and various buffers).

The agent for inducing calreticulin expression comprises a synthetic peptide having a simple structure (linear peptide chain) as an active ingredient, and thus can increase the expression level of calreticulin of genomically unstable pluripotent stem cells by such a simple process as, for example, adding the agent for inducing calreticulin expression to pluripotent stem cells such as iPS cells (typically into a medium of a culture of the stem cells). Thereby, genomic stability or genomic instability of the stem cells can be identified with high accuracy and high reliability on the basis of expression level of calreticulin of the stem cells. As the agent comprises a synthetic peptide that can be readily and artificially produced by chemical synthesis (or biosynthesis) as an active ingredient, a desired amount of the agent for inducing calreticulin expression can be readily prepared. The agent for inducing calreticulin expression can be suitably used for increasing the expression level of calreticulin particularly of genomically unstable human iPS cells.

BRIEF DESCRIPTION OF DRAWINGS

FIG. 1 is a fluorescence microscope photograph (image) for analyzing expression of calreticulin in genomically stable human iPS cells, which is an image obtained by overlaying (merging) an image of nuclear staining with DAPI (4',6-diamidino-2-phenylindole) and a fluorescence image showing the result of an immunofluorescence antibody assay using an anti-calreticulin antibody.

FIG. 2 is a fluorescence microscope photograph (image) for analyzing expression of calreticulin in a human iPS cell culture containing genomically unstable (specifically, chromosome 12 is triploid (trisomy)) cells, which is an image obtained by overlaying (merging) an image of nuclear staining with DAPI and a fluorescence image showing the result of an immunofluorescence antibody assay using an anti-calreticulin antibody.

FIG. 3 is a fluorescence microscope photograph (image) for analyzing expression of calreticulin in iPS cells in a human iPS cell culture containing genomically unstable (specifically, chromosome 12 is triploid (trisomy)) cells cultured by adding a calreticulin expression inducing peptide (sample 1) according to an embodiment so that the concentration thereof in a medium was 10 μM, which is an image obtained by overlaying (merging) an image of nuclear staining with DAPI and a fluorescence image showing the result of an immunofluorescence antibody assay using an anti-calreticulin antibody.

FIG. 4 is a fluorescence microscope photograph (image) for analyzing expression of calreticulin in genomically stable human iPS cells cultured by adding a calreticulin expression inducing peptide (sample 1) according to an embodiment so that the concentration thereof in a medium was 10 M, which is an image obtained by overlaying (merging) an image of nuclear staining with DAPI and a fluorescence image showing the result of an immunofluorescence antibody assay using an anti-calreticulin antibody.

FIG. 5 is the same image as FIG. 2, i.e. a fluorescence microscope photograph (image) for analyzing expression of calreticulin in iPS cells in a human iPS cell culture containing genomically unstable (specifically, chromosome 12 is triploid (trisomy)) cells cultured without addition of calreticulin expression inducing peptide, which is an image obtained by overlaying (merging) an image of nuclear staining with DAPI and a fluorescence image showing the result of an immunofluorescence antibody assay using an anti-calreticulin antibody.

FIG. 6 is the same image as FIG. 1, i.e. a fluorescence microscope photograph (image) for analyzing expression of calreticulin in genomically stable human iPS cells cultured without addition of calreticulin expression inducing peptide, which is an image obtained by overlaying (merging) an image of nuclear staining with DAPI and a fluorescence image showing the result of an immunofluorescence antibody assay using an anti-calreticulin antibody.

FIG. 7 is a histogram showing the result of FACS analysis of fluorescence intensity of a fluorescent dye (phycoerythrin) after immunofluorescent staining of a human iPS cell culture containing genomically unstable (specifically, chromosome 12 is triploid (trisomy)) cells using an anti-calreticulin antibody labelled with the fluorescent dye (phycoerythrin). The fluorescence intensity is indicated on the horizontal axis and the number of cells is indicated on the vertical axis. The result of a control (negative control), iPS cells without immunofluorescent staining (Unstained cells), analyzed under the same conditions as the fluorescence intensity measurement of phycoerythrin is overlaid.

FIG. 8 is a histogram showing the result of FACS analysis of fluorescence intensity of a fluorescent dye (phycoerythrin) after immunofluorescent staining of genomically stable human iPS cells using an anti-calreticulin antibody labelled with the fluorescent dye (phycoerythrin). The fluorescence intensity is indicated on the horizontal axis and the number of cells is indicated on the vertical axis. The result of a control (negative control), iPS cells without immunofluorescent staining (Unstained cells), analyzed under the same conditions as the fluorescence intensity measurement of phycoerythrin is overlaid.

DESCRIPTION OF EMBODIMENTS

Preferred embodiments of the present invention are described below. Note that matters other than the matters particularly mentioned in the present description (e.g. primary structures or chain length of synthetic peptides described herein) which are required for carrying out the present invention (e.g. general matters relating to peptide chemical synthesis, cell culture and preparation of a pharmaceutical composition including a peptide) are matters of design variation that could be apprehended by a person skilled in the art based on conventional art in such fields as cell engineering, physiology, medical science, pharmaceutical science, organic chemistry, biochemistry, gene engineering, protein engineering, molecular biology, genetics and the like. The present invention can be practiced based on the technical details disclosed in the present description and common general technical knowledge in the pertinent fields. In the following description, amino acids are indicated by single-letter designations (in sequence listings, by three-letter designations) in accordance with the nomenclature for amino acids set forth in the IUPAC-IUB guidelines.

The contents of all publications cited herein are incorporated herein by reference.

In the present description, the term "synthetic peptide" refers to a peptide fragment that is produced by artificial chemical synthesis or biosynthesis (i.e. genetic engineering based production) and may stably exist in a certain composition (e.g. an agent for inducing calreticulin expression), rather than one of which the peptide chain stably exists by itself in nature.

In the present description, the term "peptide" denotes an amino acid polymer having a plurality of peptide bonds. The term is not limited by the number of amino acid residues in a peptide chain, and refers to a chain having relatively small molecular weight typically including the one having about 100 or less (preferably 60 or less, for example 50 or less) amino acid residues in total.

In the present description, unless otherwise specified, the term "amino acid residue" includes the N-terminal amino acid and the C-terminal amino acid of a peptide chain.

The amino acid sequences described herein are always denoted as N-terminal on the left side and C-terminal on the right side.

In the present description, the term "modified amino acid sequence" with regard to a prescribed amino acid sequence refers to an amino acid sequence obtained by substituting, deleting and/or adding (inserting) one or a few (e.g. 2 or 3) amino acid residues without a loss of the function of the prescribed amino acid sequence (e.g. calreticulin expression inducing activity of the calreticulin expression inducing peptide). Typical examples encompassed by such modified amino acid sequence as used herein include a sequence obtained by so-called conservative amino acid replacement, i.e. conservative substitution of 1 or a few (typically 2 or 3) amino acid residues (e.g. a sequence wherein a basic amino acid residue has been replaced with another basic amino acid residue: e.g. replacement between a lysine residue and an arginine residue), or a sequence wherein 1 or a few (typically 2 or 3) amino acid residues are added (inserted) or deleted to/from a prescribed amino acid sequence. Accordingly, the calreticulin expression inducing peptide described herein encompasses synthetic peptides having identical amino acid sequences as those represented by corresponding SEQ ID NOs as well as synthetic peptides having amino acid sequences wherein 1 or a few (typically 2 or 3) amino acid residues are replaced (e.g. conservative amino acid replacement as described above), deleted and/or added in/from/to amino acid sequences represented by SEQ ID NOs and which still exhibit the calreticulin expression inducing activity.

In the present description, the term "pluripotent stem cell" refers to a stem cell that has an ability to differentiate to various types of cells that form an organism except for extraembryonic tissues such as placenta and has replication competence when the cell is undifferentiated. Examples thereof include ES cells, iPS cells and EG cells (embryonic germ cells). Particularly, the term "induced pluripotent stem cell (iPS cell)" refers to a cell that has pluripotency and replication competence by artificially initialising (reprogramming) a differentiated cell (typically a somatic cell such as a skin fibroblast). Examples of the method for initialising differentiated cells include a method wherein several initialising factors (e.g. four genes of Oct3/4, klf4, c-Myc and Sox2 or four genes of Oct3/4, Sox2, Nanog and Lin28) are introduced into the cells. The iPS cells may be engineered by molecular biological means (e.g. incorporation of marker genes for labelling calreticulin expression, incorporation of reporter genes, incorporation of expression vectors of protein fused to fluorescent proteins) as far as they retain the properties of pluripotent stem cells as described above.

The iPS cells as used herein may be derived from any source without limitation. However, human iPS cells are particularly preferable subjects of the present invention because the cells are highly valuable for application in the medical industry.

In the present description, terms "genomic stability" and "genomic instability" have broad meanings and are the terms that may be used to classify by stability or instability using the presence or absence or extent of genomic structural and/or functional aberration typically including those described hereinafter as an index. For example, genomic stability or genomic instability can be identified on the basis of the presence or absence or extent of a local aberration of DNA base sequences (e.g. base substitution, point mutation, gene duplication, DNA region shuffling between genes or gene horizontal transfer), a chromosome aberration (e.g. a partial chromosome aberration such as partial duplication, inversion, deletion, translocation or cleavage, a chromosome aberration in terms of the number thereof such as aneuploid, or multinucleation) or an epigenetic aberration (change in DNA methylation, change in histone modification, change in chromatin structure, or change in non-translated RNA). Classification of genomic stability or genomic instability suitable for the present invention may use a chromosome aberration as an index. The chromosome aberration as used herein may encompass so-called "karyotype aberration". Among chromosome aberrations, genomic stability or genomic instability may be classified (evaluated) particularly according to the presence or absence or extent of an aneuploid, preferably a duplication aberration, still more preferably duplication of chromosome 12.

The method for evaluating genomic stability of pluripotent stem cells (typically an iPS cell culture or an ES cell culture) derived from humans or a mammal other than humans described herein is characterized in that the method includes preparing a culture of interest containing pluripotent stem cells such as iPS cells, and analyzing the expression level of calreticulin (typically the calreticulin abundance on cell membrane of the pluripotent stem cells of interest) for pluripotent stem cells (e.g. a whole or partial population of pluripotent stem cells in the culture or individual pluripotent stem cell) in the culture followed by identifying genomic stability or genomic instability of the pluripotent stem cells of interest on the basis of the expression level of calreticulin. As genomically unstable pluripotent stem cells such as iPS cells have a significantly increased expression level of calreticulin compared to genomically stable pluripotent stem cells, analysis of the expression level of calreticulin for pluripotent stem cells in a culture allows identification of genomic stability or instability of the stem cells.

In the pluripotent stem cell genomic stability evaluation method, pluripotent stem cells (typically iPS cells or ES cells), for which the expression level of calreticulin of the stem cells is above a prescribed level, are identified as genomically unstable. For example, a criterion of the expression level of calreticulin that allows identification of genomic stability or genomic instability of iPS cells to be evaluated can be established by comparing the expression level of calreticulin in iPS cells that have been found to be genomically stable (for example, including a comparative standard, for example, 201B7 clone that is commonly available as an iPS cell having normal karyotype) and/or the expression level of calreticulin in an iPS cell culture that has been found to contain genomically unstable cells (e.g. 201B2 clone that is commonly available as an iPS cell having a normal chromosome 12 which is triploid). The criterion of the expression level of calreticulin that allows identification of genomic stability or genomic instability of pluripotent stem cells may vary according to the sensitivity and accuracy of the method for measuring the expression level of calreticulin, and thus can be established according to the method for measuring which is employed. For example, pluripotent stem cells may be identified as genomically unstable when the stem cells express preferably 1.2 times or more (e.g. 1.5 times or more, more preferably 2 times or more, still more preferably 5 times or more, for example 10 times or more) calreticulin compared to the expression level of calreticulin in comparative pluripotent stem cells (e.g. iPS cells) which have been found to be genomically stable. The criterion of the expression level of calreticulin that allows identification of genomic stability or genomic instability of pluripotent stem cells to be evaluated is preferably established by using pluripotent stem cells derived from the same source.

The expression level of calreticulin in pluripotent stem cells such as iPS cells described herein may be analyzed (measured) by any method without limitation as far as the method allows qualitative or quantitative understanding of the expression level of calreticulin. Examples of the method that allows direct understanding of the expression level of calreticulin include western blotting, immunological antibody assay (typically immunohistochemistry or IHC; also referred to as immunostaining) and methods derived therefrom. Examples of the method that allows indirect understanding of expression of calreticulin from expression of calreticulin gene include northern blotting, RT-PCR, real-time PCR, in situ hybridisation and methods derived therefrom. Examples of the method that allows understanding of the expression level of calreticulin by using a label (typically a transcription product or translation product of a transgene) which has been introduced to pluripotent stem cells of interest such as iPS cells by molecular biological means as a marker (index) include reporter assay and measurement of calreticulin fused to a fluorescent protein. The methods for measuring the expression level of calreticulin described above are merely examples that do not limit the present invention. The method for measuring the expression level of calreticulin described above may be used alone or in combination of two or more methods.

Genomic stability or instability of pluripotent stem cells (e.g. iPS cells) may be suitably identified by an immunological assay (e.g. western blotting or immunological antibody assay) using an antibody specifically reacting with calreticulin or a fragment thereof (i.e. anti-calreticulin antibody). An immunological assay using an anti-calreticulin antibody allows direct understanding of the expression level of calreticulin with high specificity and high sensitivity, and thus is preferable. Particularly, an immunological antibody assay (typically immunostaining) allows analysis of the expression level of calreticulin in pluripotent stem cells such as iPS cells while retaining the shape of the stem cells (i.e. without cell disruption or cell lysis), and thus is a suitable method when the expression level of calreticulin in individual pluripotent stem cells is sought to be understood. An immunological antibody assay (typically immunostaining) allows specific identification of calreticulin only existing on the surface of pluripotent stem cells such as iPS cells (typically the surface of cell membrane) (i.e. without being affected by the expression level of calreticulin constitutively expressed in the cells), and thus allows highly accurate identification of genomic stability or genomic instability of pluripotent stem cells.

The immunological assay typically refer to a method in which an antigen (or a fragment thereof) is reacted with an antibody that specifically reacts with the antigen to form an immunocomplex and the antibody is detected (visualised) to understand the amount of the antigen. In the present invention, both a method (direct method) in which a labelled anti-calreticulin antibody is used or a method (indirect method) in which a labelled secondary antibody that specifically recognises an anti-calreticulin antibody is used are suitably used. The indirect method allows understanding of the expression level of calreticulin with an increased sensitivity compared to the direct method, and thus is particularly preferable. An anti-calreticulin antibody may be detected (visualised) by, for example, immunofluorescence antibody assay, immunoenzymatic assay, autoradiography or colloidal gold method. For example, in an immunofluorescence antibody assay, an anti-calreticulin antibody or a secondary antibody is labelled with a fluorescent dye, colour is generated from the fluorescent dye by irradiation of excitation light after antigen-antibody reaction and the generated fluorescence is detected using a fluorescent microscope or the like. An immunofluorescence antibody assay allows understanding of the expression level of calreticulin with high accuracy, and thus is particularly preferable. The term "antibody" as used herein encompasses both monoclonal and polyclonal antibodies and is not limited by differences in immunised animals (antibody producing animals, hosts, sources) or in constant regions of immunoglobulins (also referred to as isotypes or classes).

Typically, an anti-calreticulin antibody is subjected to antigen-antibody reaction with iPS cells in an iPS cell culture and a fluorescent labelled secondary antibody directed against the anti-calreticulin antibody is then allowed to react. Thereafter, fluorescence of the fluorescent label may be detected with a fluorescent microscope or the like to understand the expression level of calreticulin in the iPS cells (typically the expression level of calreticulin present on the surface of the iPS cells).

Alternatively, a method which allows analysis of the expression level of calreticulin in pluripotent stem cells (e.g. iPS cells) of interest while the stem cells are alive (i.e. without the procedure of cell fixation) is suitable for the method for producing a culture containing pluripotent stem cells as described hereinbelow. For example, modified methods derived from immunological antibody assay or measurement of calreticulin fused to a fluorescent protein allow analysis of the expression level of calreticulin in living pluripotent stem cells (e.g. iPS cells or ES cells).

The culture of pluripotent stem cells (typically iPS cells or ES cells) derived from humans or a mammal other than humans described herein may be prepared by conventionally well-known methods without limitation. For example, the same conditions as culture conditions of ES cells may be suitably used. The presence or absence of feeder cells (e.g. SNL76/7 cells, STO cells, MEF cells) is not particularly limited. However, when the expression level of calreticulin in pluripotent stem cells in a pluripotent stem cell culture (e.g. an iPS cell culture) is analized, it is preferable to prepare the culture without using feeder cells. In order to improve adhesiveness of pluripotent stem cells such as iPS cells, it is preferable that the bottom (typically the surface to which pluripotent stem cells adhere) of a culture vessel in which pluripotent stem cells are incubated is treated (coated) with an adhesive substrate (e.g. Matrigel, extracellular matrix of decidua-derived cells, gelatine, cell adhesion proteins). For example, a commercially available medium for iPS cells is injected into a culture plate of which bottom surface is coated with Matrigel, iPS cells of interest are inoculated into the culture plate and cultured for a prescribed time, and thereby the iPS cell culture may be prepared.

Alternatively, the pluripotent stem cell genomic stability evaluation method described herein may be further suitably carried out by, prior to identification of genomic stability or genomic instability of pluripotent stem cells (typically iPS cells or ES cells) of interest, supplying, at least once, to the stem cells (typically into a medium of a culture of the stem cells) the calreticulin expression inducing peptide and carrying out the identification after culturing, for a prescribed time, the stem cell culture to which the synthetic peptide has been supplied at least once.

By supplying the calreticulin expression inducing peptide to the pluripotent stem cells (e.g. iPS cells) of interest and culturing for a prescribed time, the expression level of calreticulin in genomically unstable pluripotent stem cells can be particularly increased. Thereby the difference in the expression level of calreticulin between genomically unstable pluripotent stem cells and genomically stable pluripotent stem cells can be more unambiguous than the difference obtained without addition of the calreticulin expression inducing peptide. Thus, identification of genomic stability or genomic instability of pluripotent stem cells based on the expression level of calreticulin can be carried out with high accuracy and high reliability.

The calreticulin expression inducing peptide can significantly increase the expression level of calreticulin in genomically unstable human iPS cells. Therefore, the iPS cell genomic stability evaluation method described herein can be suitably carried out particularly on human iPS cells.

The incubation time of a culture of pluripotent stem cells (e.g. iPS cells) of interest after addition of the calreticulin expression inducing peptide to the culture is not particularly limited as far as expression of calreticulin can be induced or the expression level of calreticulin can be increased in genomically unstable pluripotent stem cells. Typically, the incubation is carried out for a few hours to a few days. The incubation may be carried out for, for example, 2 hours or more, preferably 24 hours or more, more preferably 48 hours or more and the incubation may be carried out for 3 to 5 days or 6 to 7 days or about 10 days after initiation of the incubation.

As described above, the calreticulin expression inducing peptide described herein is a synthetic peptide including a calreticulin expression inducing peptide sequence having either of the following amino acid sequences:

CRAKAGDPC;   (SEQ ID NO: 1)
and

CEQKQEIRC;   (SEQ ID NO: 2)

or a modified amino acid sequence formed by substitution, deletion and/or addition of 1, 2 or 3 amino acid residues in/from/to the above amino acid sequence. Specific amino acid sequences represented by SEQ ID NO: 1 and SEQ ID NO: 2 are amino acid sequences obtained by translation of an RNA sequence included in siRNA of human centrin 2 (hereinafter also referred to as "centrin 2 siRNA-related sequences") and are the sequences for which an ability to induce expression of calreticulin or increase the expression level of calreticulin in genomically unstable pluripotent stem cells such as iPS cells was found for the first time by the inventor of the present invention.

Centrin as used herein is a centrosome-related protein which is found in the centrosome of eukaryotes and is a constituent protein of centriole involved in replication of centriole and microtubule severing. Centrin 2 is one of proteins in the centrin family (typically centrin 1, centrin 2, centrin 3 and the like) (see Non Patent Literature 3).

Typical modified amino acid sequences of the human centrin 2 siRNA-related sequence include the following amino acid sequences:

RAKAGDP;   (SEQ ID NO: 3)
and

EQKQEIR.   (SEQ ID NO: 4)

The amino acid sequences represented by SEQ ID NO: 3 and SEQ ID NO: 4 are amino acid sequences represented by SEQ ID NO: 1 and SEQ ID NO: 2 from which N-terminal and C-terminal cysteine residues (C) are deleted. The modified amino acid sequences of the centrin 2 siRNA-related sequence described herein also suitably act as the calreticulin expression inducing peptide sequence. The modified amino acid sequences represented by SEQ ID NO: 3 and SEQ ID NO: 4 are merely examples and it is not intended to limit the modified amino acid sequence of the centrin 2 siRNA-related sequence which can be used to those exemplified sequences.

Alternatively, the calreticulin expression inducing peptide described herein may be a synthetic peptide solely consisting of the calreticulin expression inducing peptide sequence represented by SEQ ID NO: 1 or SEQ ID NO: 2 or a modified amino acid sequence thereof. However, in view of improving calreticulin expression inducing activity, the synthetic peptide preferably has a membrane-penetrating peptide sequence N-terminal or C-terminal to the calreticulin expression inducing peptide sequence. The synthetic peptide having the membrane-penetrating peptide sequence is readily introduced into target pluripotent stem cells (e.g. iPS cells) and thus can have an improved calreticulin expression inducing activity.

The membrane-penetrating peptide sequence used is not particularly limited as far as it is an amino acid sequence included in a membrane-penetrating peptide that can penetrate cell membrane and/or nuclear membrane. Among various suitable known membrane-penetrating peptide sequences, the membrane-penetrating peptide sequence of the calreticulin expression inducing peptide preferably has an amino acid sequence (including modified amino acid sequences) relating to NoLSs (nucleolar localization signals). Examples thereof include amino acid sequences of the NoLS in LIM kinase 2 represented by SEQ ID NO: 5 and the NoLS in the N protein (nucleocapsid protein) of IBV (avian infectious bronchitis virus) represented by SEQ ID NO: 6. Other examples of the membrane-penetrating peptide sequence include amino acid sequences represented by SEQ ID NOs: 7 to 9 and modified amino acid sequences thereof (only those retaining membrane-penetrating ability). SEQ ID NO: 7 represents an amino acid sequence of a membrane-penetrating peptide sequence in TAT of HIV (Human Immunodeficiency Virus). SEQ ID NO: 8 represents an amino acid sequence of a membrane-penetrating peptide sequence obtained by modification of TAT (PTD4). SEQ ID NO: 9 represents an ANT-related amino acid sequence of Antennapedia, which is a mutant from *Drosophila*.

Above membrane-penetrating peptide sequences indicated also in the sequence listing are merely examples and do not limit the peptide sequences which may be used. Various membrane-penetrating peptide sequences which may be used for the present invention are disclosed in numerous references which are already published at the time of filing of the present application. Amino acid sequences of the membrane-penetrating peptide sequences are readily known by common search means.

Particularly, the membrane-penetrating peptide sequence is preferably the amino acid sequence (including a modified amino acid sequence) represented by SEQ ID NO: 5, which is also disclosed in Patent Literature 1. The membrane-penetrating peptide sequence represented by SEQ ID NO: 5 may provide, when it is combined with the calreticulin expression inducing peptide sequence (SEQ ID NO: 1 or 2) or a modified amino acid sequence thereof, a synthetic peptide having high calreticulin expression inducing activity.

The calreticulin expression inducing peptide described herein preferably include any amino acid sequence selected from the following amino acid sequences:

KKRTLRKNDRKKRGGCRAKAGDPC;   (SEQ ID NO: 10)

KKRTLRKNDRKKRGGCEQKQEIRC;   (SEQ ID NO: 11)

KKRTLRKNDRKKRGGRAKAGDP;   (SEQ ID NO: 12)
and

KKRTLRKNDRKKRGGEQKQEIR;   (SEQ ID NO: 13)

or a modified amino acid sequence of the selected amino acid sequence. The amino acid sequences represented by SEQ ID NO: 10 and SEQ ID NO: 11 are amino acid sequences having 24 amino acid residues in total constituted by combining the human centrin 2 siRNA-related sequences represented by SEQ ID NO: 1 and SEQ ID NO: 2 with the amino acid sequence derived from NoLS of LIM kinase 2 represented by SEQ ID NO: 5 via a linker consisting of 2 glycine (G) residues. The amino acid sequences represented by SEQ ID NO: 12 and SEQ ID NO: 13 are amino acid sequences having 22 amino acid residues in total constituted by combining typical modified amino acid sequences of the human centrin 2 siRNA-related sequences represented by SEQ ID NO: 3 and SEQ ID NO: 4 with the amino acid sequence derived from NoLS of LIM kinase 2 represented by SEQ ID NO: 5 via a linker consisting of 2 glycine (G) residues.

Some peptide chains (amino acid sequences) of the calreticulin expression inducing peptide described herein may be constituted by appropriately combining the calreticulin expression inducing peptide sequence and the membrane-penetrating peptide sequence described above. Any of the calreticulin expression inducing peptide sequence and the membrane-penetrating peptide sequence may be arranged relatively at the C-terminal side (the N-terminal side). It is preferable that the calreticulin expression inducing peptide sequence and the membrane-penetrating peptide sequence are arranged adjacent. Namely, it is preferred that no or 1 to 3 amino acid residues, if any, intervene between the calreticulin expression inducing peptide sequence and the membrane-penetrating peptide sequence. For example, 1 or a few (typically 2 or 3) amino acid residues (e.g. 1 or a few glycine (G) residues) functioning as a linker may be included between the calreticulin expression inducing peptide sequence and the membrane-penetrating peptide sequence.

The calreticulin expression inducing peptide described herein preferably has at least one amidated amino acid residue. Amidation of a carboxyl group of an amino acid residue (typically a C-terminal amino acid residue of a peptide chain) can improve the structural stability (e.g. protease resistance) of a synthetic peptide.

The calreticulin expression inducing peptide may contain a partial sequence (amino acid residue) other than amino acid sequences of the calreticulin expression inducing peptide sequence and the membrane-penetrating peptide sequence unless it deteriorates calreticulin expression inducing activity. The partial sequence is preferably, but is not limited to, a sequence capable of maintaining three-dimensional shape (typically a linear shape) of the calreticulin expression inducing peptide sequence and the membrane-penetrating peptide sequence. The total number of amino acid residues in the peptide chain of the calreticulin expression inducing peptide is suitably 100 or less, desirably 60 or less and preferably 50 or less. A synthetic peptide having, for example, 30 or less amino acid residues is particularly preferred.

Such a short peptide is easily synthesized by chemical synthesis and thus the calreticulin expression inducing peptide can be easily provided. The conformation of the peptide is not particularly limited as far as the peptide exhibits calreticulin expression inducing activity in an environment (in vitro or in vivo) where the peptide is used; however, the peptide is preferably linear or helix because such peptide rarely acts as an immunogen (antigen). It is difficult for the peptide having such a shape to form an epitope. In view of this, the calreticulin expression inducing peptide used for the present invention suitably is linear and has relatively low molecular weight (typically 60 or less (particularly 30 or less) amino acid residues).

The proportion of the calreticulin expression inducing peptide sequence and the membrane-penetrating peptide sequence relative to the whole amino acid sequence (i.e. % by number of amino acid residues of the calreticulin expression inducing peptide sequence and the membrane-penetrating peptide sequence relative to the total number of amino acid residues of the peptide chain) is not particularly limited unless it deteriorates calreticulin expression inducing activity. However, the proportion is desirably about 60% or more, preferably 80% or more and particularly preferably 90% or more. A preferable embodiment is a peptide consisting of the calreticulin expression inducing peptide sequence and the membrane-penetrating peptide sequence (i.e. these sequences account for 100% of the whole amino acid sequence).

The amino acid residues included in the calreticulin expression inducing peptide of the present invention are preferably all L-amino acids. However, some or all amino acid residues may be substituted with D-amino acids unless it deteriorates calreticulin expression inducing activity.

The calreticulin expression inducing peptide described herein can be easily produced according to common chemical synthesis methods. For example, conventional solid phase synthesis or liquid phase synthesis may be used. A solid phase synthesis in which an amino protecting group of Boc (t-butyloxycarbonyl) or Fmoc (9-fluorenylmethoxycarbonyl) is used is suitable.

The calreticulin expression inducing peptide described herein may be synthesised as a desired amino acid sequence having a modified portion (C-terminal amidation and the like) by solid phase synthesis using a commercially available peptide synthesiser (e.g. available from Intavis AG, Protein Technologies and the like).

Alternatively, the calreticulin expression inducing peptide may be biosynthesised according to genetic engineering. Namely, a polynucleotide (typically DNA) having a nucleotide sequence (including an ATG initiation codon) encoding an amino acid sequence of a desired calreticulin expression inducing peptide is synthesised. A recombinant vector is then constructed depending on a host cell, that has an expression gene construct comprising the synthesised polynucleotide (DNA) and various regulation elements (encompassing a promoter, a ribosome-binding site, a terminator, an enhancer and various cis elements controlling expression level) for expressing the amino acid sequence in the host cell.

The recombinant vector is introduced into the host cell (e.g. yeast, insect cells, plant cells) by common technique and the host cell or a tissue or individual comprising the cell is cultured under a prescribed condition. Thereby a desired peptide may be expressed and produced in cells. The peptide may be isolated from the host cells (from a medium when the peptide is secreted) and optionally refolded and purified to give a desired calreticulin expression inducing peptide.

Construction of a recombinant vector, introduction of the constituted recombinant vector into a host cell and the like may be carried out by methods conventionally used in the art. As the present invention is not characterized by the methods per se, detailed explanations for the methods are not given herein.

For example, a fusion protein expression system can be used in order to allow efficient production at a high amount in host cells. Thus, a gene (DNA) encoding an amino acid sequence of a desired calreticulin expression inducing peptide is chemically synthesised, and the synthesised gene is introduced into a suitable site of an appropriate vector for fusion protein expression (e.g. vectors for GST (Glutathione S-transferase) fusion protein expression such as of pET series available from Novagen and of pGEX series available from Amersham Biosciences). A host cell (typically *Escherichia coli*) is then transformed with the vector. The resulting transformant is cultured to prepare a desired fusion protein. The protein is then extracted and purified. The resulting purified fusion protein is then cleaved with a predetermined enzyme (protease) and the released desired peptide fragment (designed calreticulin expression inducing peptide) is recovered by affinity chromatography or the like. Optionally, refolding may be carried out according to an appropriate method. By using such a conventionally known fusion protein expression system (e.g. a GST/His system available from Amersham Biosciences may be used), the calreticulin expression inducing peptide described herein may be produced.

Alternatively, a desired polypeptide may be synthesized in vitro with a so-called cell-free protein synthesis system by constructing a template DNA (i.e. a synthetic gene fragment including a nucleotide sequence encoding an amino acid sequence of the calreticulin expression inducing peptide) for a cell-free protein synthesis system and using various compounds (ATP, RNA polymerase, amino acids and the like) required for peptide synthesis. With regard to cell-free protein synthesis systems, publications by Shimizu et al. (Shimizu et al., Nature Biotechnology, 19, 751-755 (2001)) and by Madin et al. (Madin et al., Proc. Natl. Acad. Sci. USA, 97(2), 559-564 (2000)) may be referred. Based on the techniques disclosed in the publications, many companies have already provided custom polypeptide production at the time of filing of the present application. In addition, cell-free protein synthesis kits are commercially available (e.g. a PROTEIOS™ Wheat germ cell-free protein synthesis kit available from Toyobo Co., Ltd., Japan).

A single- or double-stranded polynucleotide comprising a nucleotide sequence encoding the calreticulin expression inducing peptide described herein and/or a complementary nucleotide sequence thereof may be readily produced (synthesised) according to conventionally well-known methods. Namely, a nucleotide sequence corresponding to an amino acid sequence of the calreticulin expression inducing peptide may be readily determined and provided by selecting codons corresponding to the amino acid residues of the designed amino acid sequence. Once the nucleotide sequence is determined, a polynucleotide (single strand) corresponding to the desired nucleotide sequence may be readily obtained by using a DNA synthesiser and the like. The resulting single-stranded DNA may be then used as a template to obtain a desired double-stranded DNA by employing various enzymatic synthesis means (typically PCR). The polynucleotide may be in the form of DNA or RNA (such as mRNA). DNA may be provided as a double or single strand. When DNA is a single strand, it may be a coding strand (sense strand) or a non-coding strand (anti-sense strand) complementary to the coding strand.

The thus obtained polynucleotide may be used as a material for constructing a recombinant gene (expression cassette) for producing the calreticulin expression inducing peptide in various host cells or by cell-free protein synthesis systems described above.

The calreticulin expression inducing peptide described herein may be in the form of a salt unless it deteriorates calreticulin expression inducing activity in pluripotent stem cells (typically iPS cells or ES cells). For example, an acid addition salt of the peptide obtained by addition reaction with an inorganic acid or an organic acid which are generally used according to conventional methods may be used. Alternatively, the peptide may be other salts (e.g. a metal salt) as far as calreticulin expression inducing activity in pluripotent stem cells is exhibited. Thus, the "peptide" described herein and in claims encompasses the ones in the form of salts.

The agent for inducing calreticulin expression described herein may include various carriers depending on the usage forms as far as calreticulin expression inducing activity of the calreticulin expression inducing peptide, which is an active ingredient, is retained without elimination. The carrier is preferably the one generally used for peptide medicines such as a diluent and a vehicle. Although it may appropriately vary according to the application and form of the agent for inducing calreticulin expression, the carrier typically includes water, physiological buffers and various organic solvents. The carrier may be an alcohol (such as ethanol) aqueous solution at an appropriate concentration, glycerol or a non-drying oil such as olive oil. The carrier may alternatively be a liposome. An auxiliary component which may be included in the agent for inducing calreticulin expression includes various fillers, bulking agents, binding agents, wetting agents, surfactants, dyes, flavours and the like.

The form of the agent for inducing calreticulin expression is not particularly limited. Examples of the typical form include solutions, suspensions, emulsions, aerosols, foams, granules, powders, tablets, capsules, ointments, water-based gels and the like. The agent may be freeze-dried substances or granules which are dissolved in saline or appropriate buffers (e.g. PBS, namely phosphate buffered saline) immediately prior to use to prepare drug solutions and the like.

The drug (composition) in various forms may be prepared according to conventionally well-known methods from the calreticulin expression inducing peptide (principal component) and various carriers (auxiliary components). As the present invention is not characterized by such preparation methods per se, detailed explanations for the methods are not given herein. Detailed information on formulation may be found in, for example, Comprehensive Medicinal Chemistry, Corwin Hansch Ed., published by Pergamon Press (1990), the entire content of which is incorporated herein by reference.

The agent for inducing calreticulin expression (i.e. the calreticulin expression inducing peptide) described herein may be used for a method or at a dose according to the form or purpose thereof.

For example, an appropriate amount of the agent for inducing calreticulin expression (i.e. the calreticulin expression inducing peptide) described herein may be added to a medium of pluripotent stem cells (typically iPS cells or ES cells) cultured (subcultured) in vitro at any stage (preferably before evaluation of genomic stability) during cultivation. The amount and frequency of addition may vary according to the type and status of pluripotent stem cells, the cell density (cell density at the time of initiation of the culture), the passage number, the culture conditions, the type of the medium and the like conditions, and thus are not particularly limited. Typically, the agent is preferably added 1 to several times (e.g. added at initiation of the culture and additionally supplemented at the time of subculture or exchange of media) so as to obtain the peptide concentration in the medium of about 0.1 µM to 100 µM, preferably 0.5 µM to 20 µM (e.g. 1 µM to 10 µM).

The agent for inducing calreticulin expression (i.e. the calreticulin expression inducing peptide) described herein may be used in combination with other compounds that can enhance other properties (i.e. properties of pluripotent stem cells except for the expression level of calreticulin) of pluripotent stem cells that can be used for evaluation of genomic stability and/or other methods for enhancing those other properties.

The method for removing genomically unstable pluripotent stem cells from a pluripotent stem cell culture (typically an iPS cell culture or an ES cell culture) described herein is characterized in that the method includes identifying genomic stability or genomic instability of pluripotent stem cells such as iPS cells in the pluripotent stem cell culture of interest according to the pluripotent stem cell genomic stability evaluation method described herein and removing the pluripotent stem cells that have been identified as genomically unstable by the identification method from the stem cell culture.

By removing the pluripotent stem cells such as iPS cells that have been identified as genomically unstable from the pluripotent stem cell culture of interest, a pluripotent stem cell culture (e.g. an iPS cell culture) mainly containing genomically stable pluripotent stem cells can be produced. For example, a pluripotent stem cell culture can be produced in which most (e.g. 80% or more, preferably 90% or more, more preferably 98% or more) of pluripotent stem cells in the culture are genomically stable pluripotent stem cells. A preferable embodiment is a pluripotent stem cell culture in which substantially all pluripotent stem cells in the culture are genomically stable pluripotent stem cells (typically genomically stable pluripotent stem cells account for substantially 100%). Particularly, human iPS cells are highly valuable in application for the medical industry and thus are a suitable example of the pluripotent stem cells of interest.

In a pluripotent stem cell culture such as an iPS cell culture obtained by carrying out the removal method of genomically unstable pluripotent stem cells (i.e. a stem cell culture after removal of pluripotent stem cells that have been identified as genomically unstable from a pluripotent stem cell culture of interest), a pluripotent stem cell culture in which substantially all pluripotent stem cells in the culture are living cells (for example 80% or more, preferably 90% or more, more preferably 95% or more) is industrially highly valuable. Particularly, a pluripotent stem cell culture in which pluripotent stem cells in the culture are living cells (i.e. living cells account for substantially 100%) is a particularly suitable embodiment.

Examples of properties (markers, labels, indices) of pluripotent stem cells that can be used for removing pluripotent stem cells that have been identified as genomically unstable according to the pluripotent stem cell genomic stability evaluation method from a pluripotent stem cell culture (typically an iPS cell culture or an ES cells) of interest include expression of calreticulin, expression of calreticulin gene, expression of a protein or RNA highly related to expression of calreticulin, expression of a transgene introduced to pluripotent stem cells by molecular biological means, an aspect of a chromosome (e.g. chromosome aberration, multinucleation), expression of a protein or RNA of which expression level is known to vary in genomically unstable cells, physiological properties specific to genomically unstable pluripotent stem cells (proliferation, adhesion, migration, characteristic cell division, auxotrophic properties and the like) and the like. The properties of pluripotent stem cells are merely examples and are not limited thereto as far as the property is the one of pluripotent stem cells that can be used for removing pluripotent stem cells (e.g. iPS cells) that have been identified as genomically unstable according to the evaluation method from the pluripotent stem cell culture of interest. The above properties of pluripotent stem cells may be used alone or in combination of two or more properties.

Expression of calreticulin in pluripotent stem cells (e.g. iPS cells) in a pluripotent stem cell culture of interest is the same property as that of pluripotent stem cells used as a criterion of identification of genomic stability or genomic instability of pluripotent stem cells in the pluripotent stem cell genomic stability evaluation method, and thus can be suitably used in view of accurately removing pluripotent stem cells such as iPS cells that have been identified as genomically unstable according to the evaluation method from the pluripotent stem cell culture (e.g. from the iPS cell culture) of interest. Particularly, presence or absence of calreticulin on the surface of pluripotent stem cells (typically iPS cells) is preferable because it allows accurate removal of pluripotent stem cells such as iPS cells that have been identified as genomically unstable.

An index (marker, label, property) which has been used for understanding of the expression level of calreticulin of pluripotent stem cells (typically iPS cells or ES cells) in the pluripotent stem cell genomic stability evaluation method, for example, a label of an antibody used for measurement of the expression level of calreticulin, may also be used in the removal method. Utilising the same index as that used in the genomic stability evaluation method allows simplification of the procedure required for removal of pluripotent stem cells such as iPS cells that have been identified as genomically unstable, and thus is preferable.

Alternatively, expression of calreticulin can be highly specifically detected according to immunological assay (antigen-antibody reaction) using an anti-calreticulin antibody, and thus is particularly suitable in order to highly accurately and highly reliably remove pluripotent stem cells such as iPS cells that have been identified as genomically unstable. Typically, an anti-calreticulin antibody or a secondary antibody that specifically recognises an anti-calreticulin antibody may be preliminarily labelled, and pluripotent stem cells such as iPS cells that have been identified as genomically unstable may be removed with using the label as an index from a pluripotent stem cell culture (e.g. from an iPS cell culture) of interest.

The label of an antibody as described above that may be used is, for example, a fluorescent dye, magnetic beads, an affinity tag such as a GST tag and a His tag. Typically, by an immunofluorescence antibody assay using a fluorescent labelled anti-calreticulin antibody or a fluorescent labelled secondary antibody, calreticulin is labelled with fluorescence and pluripotent stem cells such as iPS cells that have been identified as genomically unstable can be highly accurately and highly reliably removed from a pluripotent stem cell culture of interest by using the fluorescent label as an index.

Alternatively, by using a transcription product or translation product of a transgene that has been introduced by molecular biological means as an index, pluripotent stem cells such as iPS cells that have been identified as genomically unstable can be effectively removed from a pluripotent stem cell culture of interest. For example, a fluorescent protein-fused calreticulin vector may be introduced into iPS cells of interest, and by using an increase in fluorescence of fluorescent protein-fused calreticulin in genomically unstable iPS cells as an index, iPS cells that have been identified as genomically unstable may be removed from the iPS cell culture of interest.

Pluripotent stem cells that have been identified as genomically unstable may be removed from a culture fluid of pluripotent stem cells of interest by removing pluripotent stem cells (e.g. iPS cells) having a certain level of a property (marker, label, index) of pluripotent stem cells used for removal that is above a prescribed level. For example, the prescribed level of the property of pluripotent stem cells that can be used for removal can be established by comparing the level of the property in pluripotent stem cells such as iPS cells that have been identified as genomically stable according to the pluripotent stem cell genomic stability evaluation method and the level of the property in pluripotent stem cells such as iPS cells that have been identified as genomically unstable. The prescribed level may vary according to the property of pluripotent stem cells employed, a method for determining (measuring) the property and the sensitivity or accuracy of the method, and thus is required to be established appropriately.

For example, by removing pluripotent stem cells having an expression level of calreticulin that is above a prescribed level from a pluripotent stem cell culture (typically from an iPS cell culture or an ES cell culture) of interest, pluripotent stem cells that have been identified as genomically unstable can be removed. The expression level of calreticulin that can be used for removal of genomically unstable pluripotent stem cells from a pluripotent stem cell culture of interest is not particularly limited as far as it allows removals of pluripotent stem cells that have been identified as genomically unstable. Typically, the expression level that may be used may be similar to the expression level of calreticulin in the genomic stability evaluation method. For example, the criterion of the expression level of calreticulin for removal of genomically unstable pluripotent stem cells may be 1.2 times or more (e.g. 1.5 times or more, more preferably 2 times or more, still more preferably 5 times or more, for example 10 times or more) of the expression level of calreticulin in genomically stable pluripotent stem cells such as iPS cells (comparative cells). The criterion of the expression level of calreticulin that can be used for removal of genomically unstable pluripotent stem cells from a pluripotent stem cell culture to be evaluated is preferably established by using pluripotent stem cells derived from the same source.

Pluripotent stem cells that have been identified as genomically unstable described herein may be removed from a pluripotent stem cell culture (typically from an iPS cell culture or an ES cell culture) of interest according to various cell sorting methods without limitation. For example, cell sorting using a fluorescence-activated cell sorter (FACS), cell isolation using a magnetic cell isolation device (MACS®), cell sorting under a microscope, cell sorting using optical forceps, cell sorting using various columns, cell sorting utilizing immunological assay (antigen-antibody reaction), cell sorting utilizing cell staining, cell sorting utilizing labelling by incorporation of specific genes, cell sorting utilizing physiological properties of cells (proliferation, adhesion, migration, characteristic cell division, auxotrophic properties and the like) may be mentioned. Particularly, a cell sorting method which utilises immunological assay using an anti-calreticulin antibody allows cell sorting with high specificity and high reliability, and thus is particularly preferable. Cell sorting methods using FACS, MACS and various columns allow selection of cells with high efficiency, and thus are preferable.

Pluripotent stem cells such as iPS cells that have been identified as genomically unstable may be removed at the same time as identification of genomic stability or genomic instability of pluripotent stem cells in the pluripotent stem cell culture of interest. Carrying out the identification and removal at the same time allows simplification of the required procedures for removal of genomically unstable pluripotent stem cells, and thus is preferable.

The cell sorter described herein used for removal of pluripotent stem cells that have been identified as genomically unstable from a pluripotent stem cell culture (typically from an iPS cell culture or an ES cell culture) of interest may be any cell sorter without limitation. Examples of the cell sorter include FACS, MACS®, cell sorters utilizing optical forceps and cell sorters utilizing various columns. FACS, MACS and cell sorters utilizing optical forceps can remove pluripotent stem cells such as iPS cells that have been identified as genomically unstable from a pluripotent stem cell culture of interest by automated systems with high efficiency, and thus are suitably used for the present invention. Particularly, FACS and MACS are preferred as they allow identification of genomic stability or genomic instability of pluripotent stem cells based on the expression level of calreticulin and removal of genomically unstable pluripotent stem cells at the same time.

Genomically unstable iPS cells may be removed by using, for example, FACS according to the following method. An anti-calreticulin antibody is allowed to react with iPS cells in an iPS cell culture of interest according to antigen-antibody reaction and a fluorescent labelled secondary antibody directed against the anti-calreticulin antibody is then allowed to react. Thereafter, fluorescence of the fluorescent label may be analyzed with FACS and iPS cells having a fluorescence intensity that is above a prescribed level may be removed from the iPS cell culture of interest, thereby removing genomically unstable iPS cells. The iPS cells having a fluorescence intensity that is above a prescribed level are cells having higher fluorescence intensity than iPS cells that have been found to be genomically stable (e.g. the 201B7 strain) or cells having a fluorescence intensity approximately at or above fluorescence intensity of genomically unstable cells in an iPS cell (e.g. 201B2 strain) culture that has been found to contain genomically unstable cells.

Typical examples of pluripotent stem cells that are removed by the removal method of genomically unstable pluripotent stem cells (e.g. iPS cells or ES cells) include pluripotent stem cells having a chromosome aberration and/or multinucleation. The pluripotent stem cells (including cells, a cell cluster, a tissue and the like obtained by induction of differentiation of the pluripotent stem cells) may cause tumours after in vivo transplantation, and thus are genomically unstable iPS cells removal of which is particularly sought from a pluripotent stem cell culture for regenerative therapy. Removal of human iPS cells having a chromosome aberration and/or multinucleation is a particularly preferable embodiment of the present invention.

A number of Examples of the present invention are hereinafter described. However, it is not intended to limit the present invention to the Examples.

In the following Examples, iPS cells were used as an example of pluripotent stem cells. Specifically, cells used for tests were a genomically stable (specifically without a chromosome aberration) human iPS cell strain (clone: 201B7, hereinafter also merely referred to as 201B7) and a human iPS cell strain (clone: 201B2 hereinafter also merely referred to as 201B2) containing genomically unstable (specifically, chromosome 12 is triploid (trisomy)) cells. Both 201B7 and 201B2 are clones of iPS cells established from the same human fibroblasts (source: Takahashi K et al., Cell, 131, 861-872 (2007)). The iPS cells were provided by the Center for iPS Cell Research and Application, Kyoto University. The iPS cells were subcultured with feeder cells, which were murine foetal fibroblasts (cell line: SNL 76/7) licenced from Baylor College of Medicine.

Example 1: Preparation of iPS Cell Culture
(Subculture of iPS Cells)

The iPS cells (201B7 and 201B2) were subcultured according to the following method to prepare cultures of iPS cells. The method is detailed as follows.

SNL76/7 cells inactivated by treatment with mitomycin C were inoculated into a culture vessel (culture dish having a diameter of 10 cm) coated with gelatine one to four days prior to the inoculation of the iPS cells (201B7 and 201B2).

The SNL76/7 cells were cultured at 5% $CO_2$ and 37° C. until immediately before the inoculation of the iPS cells. Immediately before inoculation of the iPS cells on the feeder cells, the feeder cells were washed with PBS (−) (phosphate buffered saline), and the medium was replaced with a primate ES/iPS cell medium (Primate ES Cell Medium: available from ReproCELL, hereinafter also referred to as ES medium) containing 4 ng/mL of recombinant bFGF (Recombinant Basic Fibroblast Growth Factor: available from Wako Pure Chemical Industries), thereby preparing the feeder cells.

Then, the respective iPS cells were detached with a CTK solution (0.25% trypsin solution containing 0.1 mg/mL collagenase IV (a product from Life Technologies), 1 mM calcium chloride and 20% KSR (knockout serum replacement)) to the extent that the periphery of iPS cell colonies was detached. The CTK solution was washed off with PBS (−), the ES medium was added and iPS cell colonies were then completely detached using a cell scraper. The ESC medium in the culture vessel in which iPS cell colonies were suspended was transferred to a 15-mL tube, and furthermore, the iPS cell colonies remaining in the culture vessel were flushed with the ESC medium and collected in the 15-mL tube. The 15-mL tube was left to stand for 5 minutes to precipitate the iPS cell colonies and the supernatant was removed. Thereafter, the iPS cell colonies were dispersed and suspended in a fresh ES medium using a pipette to prepare an iPS cell suspension.

An appropriate amount (e.g. ⅓ to ⅛ of the total amount of cell suspension when a culture vessel having similar volume is used for subculture) of the thus obtained iPS cell suspension was inoculated onto the feeder cells in the culture vessel prepared as described above. The culture vessel was incubated in an incubator at 5% $CO_2$ and 37° C. The medium was replaced every 1 to 2 days and culture was continued until iPS cells covered 80 to 90% of the bottom surface area of the culture vessel (i.e. 80-90% confluent). The 80-90% confluent iPS cells were repeatedly subcultured by the above method. The iPS cell cultures were thus prepared.

Example 2: Evaluation Test of Expression Level of Calreticulin in iPS Cells

Genomically stable iPS cells and genomically unstable iPS cells were examined for expression of calreticulin. Cells used for the test were two types of iPS cells (201B7 and 201B2). The evaluation test is detailed as follows.

The respective iPS cells (201B7 and 201B2) prepared by the method described in Example 1 were collected in a 15-mL tube in the same manner as the subculture described above, which was then left to stand for 5 minutes. Thereafter, the supernatant was removed, and iPS cell colonies were dispersed and suspended in a fresh mTeSR® medium (available from STEMCELL Technologies) using a pipette. The iPS cell suspension was then inoculated in an 8-well slide coated with Matrigel at a cell density of about $1\times10^4$ per well. The culture vessel was then incubated in an incubator overnight at 5% $CO_2$ and 37° C. After the overnight incubation, the medium was replaced with a fresh mTeSR® 1 medium and incubation was continued under the same conditions for a further 5 days. During the incubation period of 5 days, the medium was replaced every day.

After the incubation was completed, expression of calreticulin in the respective iPS cells (201B2 and 201B7) was examined by the immunofluorescence antibody assay (also referred to as immunofluorescent staining) described hereinbelow.

Specifically, the medium in each culture vessel of iPS cells was removed and the cells were washed with PBS (−). A mixed solution of 1 volume of methanol and 1 volume of acetone (methanol/acetone=1:1 solution) was then added and left on ice for 15 minutes to fix the iPS cells. Thereafter, the methanol/acetone=1:1 solution was removed, 3% BSA-containing PBS (−) (PBS (−) containing 3% BSA) was added and blocking was carried out at room temperature for 1 hour. After a certain amount of time, 3% BSA-containing PBS (−) was removed followed by washing with PBS (−).

A primary antibody diluted solution prepared by adjusting a primary antibody, an anti-calreticulin monoclonal [FMC75] antibody (murine, available from Abcam, Cat No. ab22683, Lot No. GR56669-4), to a final concentration of $4\times10^{-3}$ mg/mL in 1% BSA/PBS (−) (PBS (−) containing 1% BSA) was added to the culture vessel of the iPS cells, and the mixture was left to stand overnight at 4° C. or 2 hours at room temperature. After a certain amount of time for antigen-antibody reaction, the primary antibody diluted reaction was removed followed by washing with PBS (−). A secondary antibody diluted solution prepared by adjusting a secondary antibody, a fluorescent dye (Alexa® 488)-labelled anti-mouse IgG antibody (goat: available from Life Technologies, A11001), to a final concentration of $10\times10^{-3}$ mg/mL in 1% BSA/PBS (−) was then added and left to stand at room temperature for 2 hours. After a certain amount of time, the secondary antibody diluted solution was removed followed by washing with PBS (−). Thereafter, mounting was carried out with a DAPI (4′,6-diamidino-2-phenylindole)-containing mounting medium (available from Life Technologies) and a cover glass and fluorescence was observed under a confocal laser microscope.

The results are shown in FIGS. 1 and 2. These figures are fluorescence microscope photographs for analyzing expression of calreticulin in iPS cells (201B7 and 201B2), and are images respectively obtained by overlaying (merging) a fluorescence image showing the result of analysis of expression of calreticulin according to the immunofluorescence antibody assay and an image of nuclear staining with DAPI. FIG. 1 shows the result of 201B7 and FIG. 2 shows the result of 201B2.

As shown in FIG. 2 showing the fluoroimmuno microscope photograph of 201B2, intense fluorescence from the label detecting calreticulin was confirmed compared to the fluorescence microscope photograph of 201B7 in FIG. 1. Namely, the genomically unstable iPS cells (201B2) were found to have a significantly increased expression level of calreticulin compared to genomically stable iPS cells (201B7). It was concluded that a weak fluorescence of the label detecting calreticulin observed in 201B7 was calreticulin constitutively expressed in the cells. In FIG. 1, a few cells were found to have intense fluorescence of the label detecting calreticulin. The cells were confirmed to be genomically unstable iPS cells, although detailed data are now shown, and thus it was concluded that the cells corresponded to iPS cells rendered to be genomically unstable by subculture.

The results indicate that genomic stability or genomic instability of pluripotent stem cells in a culture of the pluripotent stem cells of interest can be identified on the basis of the expression level of calreticulin by analyzing the same. The results also indicate that an immunological assay can be suitably used for the identification.

Example 3: Peptide Synthesis

Synthetic peptides having amino acid sequences SEQ ID NOs: 10 to 13 were produced with the peptide synthesiser described hereinbelow. In the following descriptions, the synthetic peptides are denoted as samples 1 to 4 according to the order of the SEQ ID NOs. Table 1 indicates information on the amino acid sequences and the like of the synthetic peptides.

TABLE 1

| Sample No. | Amino acid sequence | Total amino acid residues |
|---|---|---|
| 1 | KKRTLRKNDRKKR GG CRAKAGDPC (SEQ ID NO: 10) | 24 |
| 2 | KKRTLRKNDRKKR GG CEQKQEIRC (SEQ ID NO: 11) | 24 |
| 3 | KKRTLRKNDRKKR GG RAKAGDP (SEQ ID NO: 12) | 22 |
| 4 | KKRTLRKNDRKKR GG EQKQEIR (SEQ ID NO: 13) | 22 |

As shown in Table 1, all peptides of samples 1 to 4 respectively have an amino acid sequence (SEQ ID NO: 5) derived from LIM kinase 2 at the N-terminal side of the peptide chain and respective calreticulin expression inducing peptide sequences (SEQ ID NOs: 1 to 4) C-terminal thereto via a linker region consisting of 2 glycine (G) residues.

The peptide (SEQ ID NO: 10 or 11) of sample 1 or sample 2 is a peptide having 24 amino acid residues in total having a centrin 2 siRNA-related sequence represented by SEQ ID NO: 1 or 2 as a calreticulin expression inducing peptide sequence.

The peptide (SEQ ID NO: 12 or 13) of sample 3 or sample 4 is a peptide having 22 amino acid residues in total having a typical modified sequence of a centrin 2 siRNA-related sequence represented by SEQ ID NO: 3 or 4 as a calreticulin expression inducing peptide sequence.

The synthetic peptides are linear peptides having a C-terminal amino acid of which carboxyl group (—COOH) is amidated (—CONH$_2$). The synthetic peptides were synthesized by carrying out solid phase synthesis (Fmoc method) using a commercially available peptide synthesiser (a product from Intavis AG) according to the instruction. As the present invention is not characterized by the mode of use of the peptide synthesiser per se, detailed explanation thereof is omitted.

Synthesised peptides of samples 1 to 4 were dissolved in PBS (−) to prepare peptide stock solutions.

Example 4: Evaluation of Calreticulin Expression Inducing Activity of Synthetic Peptides The peptides of samples 1 to 4 obtained in Example 3 were examined for calreticulin expression inducing activity. Cells used for the test were iPS cells (201B7 and 201B2) described above. The evaluation test is detailed as follows.

In the same manner as in Example 2, the respective iPS cells (201B7 and 201B2) were inoculated in an 8-well slide coated with Matrigel so as to be about $1 \times 10^4$ per well and incubated overnight at 5% $CO_2$ and 37° C. After the overnight incubation, the medium was replaced with a mTeSR® 1 medium containing each peptide of samples 1 to 4 at a peptide concentration of 10 μM and incubated for 5 days. During the incubation period of 5 days, the medium was replaced every day with a mTeSR® 1 medium containing each peptide of samples 1 to 4 at a peptide concentration of 10 μM. Controls were carried out as comparison without addition of peptides for respective iPS cells, of which conditions were the same as those in Example 2.

After the incubation was completed, expression of calreticulin in each experimental sample was analyzed by the immunofluorescence antibody assay using an anti-calreticulin antibody.

The results of fluorescence observation using a confocal laser microscope are shown in FIGS. 3 to 6. Similar to FIG. 1 or FIG. 2, these figures are fluorescence microscope photographs for analyzing expression of calreticulin in each experimental sample and are images respectively obtained by overlaying (merging) a fluorescence image showing the result of analysis of expression of calreticulin in the iPS cells according to the immunofluorescence antibody assay and an image of nuclear staining with DAPI. FIG. 3 shows the result for the experimental sample of 201B2 with addition of sample 1 and FIG. 4 shows the result for the experimental sample of 201B7 with addition of sample 1. FIGS. 5 and 6 are the same as FIGS. 1 and 2 and are the results for the experimental samples of 201B2 and 201B7 without addition of peptides.

As a result of the evaluation test, strong fluorescence of the label detecting calreticulin was found for 201B2 to which the synthetic peptide (calreticulin expression inducing peptide) of sample 1 was added (FIG. 3) compared to the experimental sample of the cells without addition of peptides (FIG. 5). Namely, it was found that the synthetic peptide of sample 1 significantly increased the expression level of calreticulin in genomically unstable iPS cells. Although the data is not shown, it was also found that synthetic peptides of samples 2 to 4 also increased, similar to sample 1, the expression level of calreticulin in 201B2.

On the other hand, it was found that 201B7 cultured with addition of the synthetic peptide of sample 1 (FIG. 4) had almost no increase of fluorescence of the label detecting calreticulin compared to the experimental sample of the cells without addition of peptides (FIG. 6). Namely, the difference in the expression level of calreticulin between iPS cells having different genomic stability could be clearly understood by comparing the expression level of calreticulin between 201B7 and 201B2 with addition of sample 1, rather than comparing the expression level of calreticulin between 201B7 and 201B2 without addition of peptides. Although the data is not shown, it was also found that synthetic peptides of samples 2 to 4 did not increase the expression level of calreticulin in 201B7, similar to sample 1, and that cultivation for a certain amount of time with addition of the peptides to an iPS cell culture of interest can make the difference in the expression level of calreticulin between iPS cells having different genomic stabilities unambiguous.

These results indicate that the calreticulin expression inducing peptides (i.e. agents for inducing calreticulin expression including the peptides as an active ingredient) described herein are the peptides (compositions) that can significantly increase the expression level of calreticulin in genomically unstable pluripotent stem cells (typically iPS cells). The results also indicate that addition of the calreticulin expression inducing peptides (i.e. agents for inducing calreticulin expression including the peptides as an active ingredient) described herein to pluripotent stem cells (typically iPS cells) of interest can increase and make it clear the difference in the expression level of calreticulin resulting from the difference in genomic stability of pluripotent stem cells. Accordingly, it is demonstrated that addition of the calreticulin expression inducing peptides (i.e. agents for inducing calreticulin expression including the peptides as an active ingredient) described herein to pluripotent stem cells (typically iPS cells) of interest allow highly sensitive and highly accurate identification of genomic stability or genomic instability of the stem cells on the basis of the expression level of calreticulin in the stem cells.

Example 5: Test for Removing Genomically Unstable iPS Cells from iPS Cell Culture By using the iPS cells (201B7 and 201B2), it was examined whether or not genomically unstable iPS cells could be removed from cultures of the iPS cells. The test is detailed as follows.

The iPS cell cultures were prepared as described hereinbelow. The respective iPS cells (201B7 and 201B2) prepared according to the procedure described in Example 1 were inoculated in a culture dish having a diameter of 10 mm (10-mm dish) preliminarily coated with GelTrex (a product from Life Technologies) at a cell density of about $1 \times 10^6$ cells per well (i.e. feeder cell-free). The medium used was an Essential 8® medium (a product from Life Technologies). The culture vessel was incubated in an incubator at 5% $CO_2$ and 37° C. for 5 days. During the incubation period of 5 days, the medium was replaced every day.

After the incubation was completed, calreticulin expressed on the iPS cells were labelled with fluorescence and genomically unstable cells were removed from the culture of the iPS cells using FACS with the fluorescence intensity of the label detecting calreticulin being used as an index. Specific test procedure is detailed as follows.

The iPS cells after the incubation for 5 days were treated with a ROCK (Rho-associated coiled-coil containing protein kinase/Rho-associated kinase) inhibitor. Specifically, to the medium of the iPS cells after the incubation for 5 days, a ROCK inhibitor, Y-27632, was added so that the concentration thereof in the medium was 10 μM and the cells were left to stand in an incubator at 5% $CO_2$ and 37° C. for 1 hour. From the iPS cells after the incubation in the presence of the ROCK inhibitor (treatment with the ROCK inhibitor), the medium was removed from the culture vessel and the cells were washed once with PBS.

The respective iPS cells after the treatment with the ROCK inhibitor were collected in a prescribed test tube. Specifically, 3 mL of PBS (−) containing 0.5 mM EDTA (hereinafter also referred to as "EDTA/PBS (−)") was added to the culture vessel of the respective iPS cells and the culture vessel was left to stand in an incubator at 5% $CO_2$ and 37° C. for 15 minutes. EDTA/PBS (−) was then removed from the culture vessel, 4 mL of PBS (−) was added to the culture vessel and subjected to pipetting procedure. The pipetting procedure detached iPS cells from the culture vessel and dispersed the cells in the PBS (−). The PBS (−) in which iPS cells were dispersed was collected in a 15-mL tube to which 4 mL of a primate ES/iPS cell medium (Primate ES Cell Medium: available from ReproCELL) was added. The 15-mL tube containing collected iPS was centrifuged at 120×g (wherein "xg" denotes centrifugal force and means relative centrifugal acceleration relative to the acceleration of gravity on Earth; for example, 120×g is relative acceleration (centrifugal force) that is 120 times of the acceleration of gravity on Earth; the same applies hereinafter) for 5 minutes to remove the supernatant (PBS (−) and the primate ES/iPS cell medium). The cells were then washed once with PBS containing 2% FBS (hereinafter the FBS-containing PBS may also referred to as "incubation buffer") (centrifugation: 120×g, 5 min.). The iPS cells were then dispersed in the incubation buffer containing 10 μM of Y-27632 (hereinafter also referred to as "Y-27632 (10 μM)-containing incubation buffer") and a cell dispersion having a cell density of about $1 \times 10^6$ cells/100 μL was prepared. The iPS cell dispersion was aliquoted in separately prepared 1.5-mL tubes and used for the test described hereinbelow.

According to the immunofluorescent staining (immunofluorescence antibody assay) as described hereinbelow, calreticulin on the surface of iPS cells in the respective experimental samples was then labelled with fluorescence.

The anti-calreticulin antibody used was an antibody labelled with phycoerythrin (hereinafter the fluorescent dye is also referred to as "PE") (i.e. fluorescent PE-labelled antibody), an anti-calreticulin monoclonal [FMC75]-phycoerythrin antibody (murine, available from Abcam, Cat No. ab83220, Lot No. GR177933-2). As an isotype control of the anti-calreticulin monoclonal [FMC75]-phycoerythrin antibody, a fluorescent PE-labelled antibody, a Mouse IgG1 (PE)-Isotype control (murine, available from Abcam, Cat No. ab81200, Lot No. GR183088-1) was used. An antibody diluted solution obtained by adjusting the anti-calreticulin antibody (or the isotype control) in Y-27632 (10 μM)-containing incubation buffer to a final concentration of 10 μg/mL was added to each test tube which was then left to stand in the dark at 4° C. for 1.5 hours. After the antigen-antibody reaction for a prescribed amount of time, the antibody diluted solution was removed by centrifugation at 130×g for 5 minutes and the iPS cells were washed twice with 1 mL of incubation buffer (centrifugation: 130×g, 5 min.). The iPS cells were then washed once with 300 μL of On-Chip Sample Buffer (available from On-chip Biotechnologies Co., Ltd.) (centrifugation: 260×g, 5 min.). The iPS cells were then dispersed in the On-Chip Sample Buffer to prepare a cell dispersion having a cell density of at least $5 \times 10^5$ cells/100 μL.

As described above, in the immunofluorescent staining, cell fixation and permeabilization were not carried out. Namely, calreticulin on the cell surface was specifically stained by a immunofluorescent manner using the anti-calreticulin antibody.

The iPS cells in each experimental sample after immunofluorescent staining were then subjected to selection of genomically unstable iPS cells based on the result of the analysis of the abundance of calreticulin on the cell surface using FACS. Namely, the fluorescence intensity (excitation wavelength: 488 nm, maximum fluorescence wavelength: 575 nm) of the fluorescent dye (phycoerythrin) detecting calreticulin was analyzed and iPS cells were selected (genomically unstable iPS cells were removed) on the basis of the intensity of the fluorescent label. As the FACS, On-Chip Sort available from On-chip Biotechnologies Co., Ltd. was used.

The results of FACS analysis (measurement) of the fluorescence intensity (excitation wavelength: 488 nm, maximum fluorescence wavelength: 575 nm) of the fluorescent dye (phycoerythrin) detecting calreticulin for the iPS cells (201B2 and 201B7) in the respective experimental samples (experimental samples stained with the anti-calreticulin antibody) after immunofluorescent staining with the anti-calreticulin antibody are shown in FIG. 7 (the result for 201B2) and FIG. 8 (the result for 201B7). In FIGS. 7 and 8, the results for the experimental samples (experimental samples stained with the anti-calreticulin antibody) are indicated as "PE-Anti-Calreticulin antibody-stained cells". These figures are histograms showing the fluorescence intensity of the cells, wherein the fluorescence intensity is indicated on the horizontal axis and the number of cells is indicated on the vertical axis.

As a control (negative control), iPS cells without immunofluorescent staining (Unstained cells) were analyzed under the same conditions as the fluorescence intensity measurement of phycoerythrin as described above. The results for the Unstained cells are overlaid on the histograms (FIG. 7 and FIG. 8) showing the fluorescence intensity for the experimental samples after immunofluorescent staining using the anti-calreticulin antibody. The results of those experimental samples (negative controls) are indicated in FIG. 7 and FIG. 8 as "Unstained cells (Negative control)".

It is inferred that the peaks found in the fluorescence intensity histogram for the negative control samples were due to detection of autofluorecence of the cells. Although detailed data is not shown, it was confirmed that, by comparison between the fluorescence intensity histogram for the negative control sample and the fluorescence intensity histogram for the experimental sample after immunofluorescent staining using the isotype control, the iPS cells of 201B2 and 201B7 had almost the same peaks in the histograms. Namely, it was confirmed that the anti-calreticulin antibody (anti-calreticulin monoclonal [FMC75]-phycoerythrin antibody) used in the present test results in extremely low non-specific antigen-antibody reaction with iPS cells.

As shown in FIG. 7, for the culture of iPS cells (201B2) containing genomically unstable cells, it was found that, by comparison between the fluorescence intensity histogram for the experimental sample stained with the anti-calreticulin antibody and the fluorescence intensity histogram for the negative control sample of the cells, the gradient on the right hand side (i.e. on the side of higher fluorescence intensity) of the top of the peak in the fluorescence intensity histogram for the experimental sample stained with the anti-calreticulin antibody is less steep than the peak found in the fluorescence intensity histogram for the negative control sample and the phases are not in conformity. Namely, it was found that the experimental sample stained with the anti-calreticulin antibody contained a cell population having a higher fluorescence intensity than the cells in the negative control sample. The cell population having high fluorescence intensity expresses a high amount of calreticulin on the cell surface. By using a cell sorting function of the FACS used for the present test, the cell population having a higher fluorescence intensity than the cells in the negative control sample can be selected from the cells in the experimental sample stained with the anti-calreticulin antibody to remove genomically unstable cells from the cell culture of the iPS cells (201B2).

Meanwhile, as shown in FIG. 8, genomically stable iPS cells (201B7) showed almost the same position of the peaks and the same shape of the peaks between the fluorescence intensity histogram for the experimental sample stained with the anti-calreticulin antibody and the fluorescence intensity histogram for the negative control sample of the cells. Namely, it was found that the expression level of calreticulin on the surface of genomically stable iPS cells (201B7) was extremely low.

From the above results, it was found that it was possible to analyze the expression level of calreticulin in iPS cells (typically on the surface of the cells) in an iPS cell culture and identify the iPS cells having an expression level of calreticulin that is above a certain level as genomically unstable. It was also found that genomically unstable iPS cells could be removed from an iPS cell culture of interest on the basis of the expression level of calreticulin in iPS cells. The evaluation of genomic stability of iPS cells and removal of genomically unstable iPS cells could be carried out at the same time by using the same label (typically a fluorescent label of an antibody) as an index.

Although detailed data is not shown herein, it was found that expression of calreticulin on the surface of genomically unstable cells could be increased by adding, prior to the analysis of the expression level of calreticulin, a calreticulin expression inducing peptide (i.e. an agent for inducing calreticulin expression including the peptide as an active ingredient) to an iPS cell culture, and thus the genomically unstable iPS cells could be removed with high accuracy and high reliability.

Example 6: Preparation of Granules

Each of the synthetic peptides (calreticulin expression inducing peptides, 50 mg) of samples 1 to 4, 50 mg of crystalline cellulose and 400 mg of lactose were mixed, followed by addition of 1 mL of a mixed solution of ethanol and water and further mixing. The mixed substance was granulated according to the standard method to obtain granules (a granular composition) containing the calreticulin expression inducing peptides described herein as a principal component.

INDUSTRIAL APPLICABILITY

As described above, according to the method for evaluating genomic stability of pluripotent stem cells described herein allows identification of genomic stability of pluripotent stem cells (typically iPS cells or ES cells) with high efficiency and high reliability, and thus can be utilised for, for example, chromosome analysis of pluripotent stem cells (preferably iPS cells). According to the removal method of genomically unstable pluripotent stem cells described herein, a pluripotent stem cell culture (typically an iPS cell culture or an ES cell culture) from which pluripotent stem cells that have been identified as genomically unstable have been removed can be provided (produced). The pluripotent stem cell culture can be used as, for example, a suitable medical material for regenerative therapy. The calreticulin expression inducing peptide and the agent for inducing calreticulin expression including the peptide as an active ingredient have calreticulin expression inducing activity, i.e. an activity that increases the expression level of calreticulin (or induces expression of calreticulin) in genomically unstable pluripotent stem cells (typically iPS cells), and thus can be suitably used for, for example, the pluripotent stem cell genomic stability evaluation method described above, the method for removing genomically unstable pluripotent stem cells from a pluripotent stem cell culture described above and the method for producing a pluripotent stem cell culture from which genomically unstable pluripotent stem cells have been removed.

SEQUENCE LISTING FREE TEXT

SEQ ID NOs: 1 to 13: Synthetic peptides

The invention claimed is:

1. A method for evaluating genomic stability of pluripotent stem cells of interest derived from humans or a mammal other than humans, comprising:
preparing a culture of the pluripotent stem cells;
supplying, at least once, to the pluripotent stem cell culture of interest a synthetic peptide comprising a calreticulin expression inducing peptide sequence consisting of either of the following amino acid sequences:

```
                                        (SEQ ID NO: 1)
    CRAKAGDPC;
    and (SEQ ID NO: 2)
    CEQKQEIRC;
``` or a modified amino acid sequence formed by substitution, deletion or addition of 1, 2 or 3 amino acid residues in/from/to the above amino acid sequences; and
analyzing an expression level of calreticulin for the pluripotent stem cells in the culture followed by identifying genomic stability or instability of the pluripotent stem cells on the basis of the expression level of calreticulin,
wherein in the identification, pluripotent stem cells, for which the expression level of calreticulin of the stem cells is 1.2 times or more compared to the expression level of calreticulin in comparative genomically stable pluripotent stem cells, are identified as genomically unstable.

2. The method according to claim 1, wherein the identification of genomic stability or instability of the pluripotent stem cells based on the expression level of calreticulin is carried out by an immunological assay using an antibody specifically reacting with calreticulin or a fragment thereof.

3. The method according to claim 1, wherein the modified amino acid sequence is an amino acid sequence of SEQ ID NO: 1 or 2 from which N-terminal and C-terminal cysteine residues (C) are deleted.

4. The method according to claim 1, wherein the synthetic peptide comprises a membrane-penetrating peptide sequence N-terminal or C-terminal to the calreticulin expression inducing peptide sequence.

5. The method according to claim 4, wherein the synthetic peptide comprises the membrane-penetrating peptide sequence consisting of the following amino acid sequence:

```
                                        (SEQ ID NO: 5)
    KKRTLRKNDRKKR.
```

6. The method according to claim 1, wherein the synthetic peptide has 30 or less amino acid residues in total.

7. The method according to claim 6, wherein the synthetic peptide comprised any of the following amino acid sequences:

```
                                        (SEQ ID NO: 10)
    KKRTLRKNDRKKRGGCRAKAGDPC;

(SEQ ID NO: 11)
    KKRTLRKNDRKKRGGCEQKQEIRC;

(SEQ ID NO: 12)
    KKRTLRKNDRKKRGGRAKAGDP;
    and (SEQ ID NO: 13)
    KKRTLRKNDRKKRGGEQKQEIR.
```

8. The method according to claim 1, further comprising:
removing the pluripotent stem cells that have been identified as genomically unstable method from the culture of the pluripotent stem cells.

9. The method according to claim 8, wherein the pluripotent stem cells that have been identified as genomically unstable are removed by using a cell sorter.

10. The method according to claim 8, wherein the genomically unstable pluripotent stem cells are pluripotent stem cells having a chromosome aberration.

11. An artificially synthesised peptide exhibiting calreticulin expression inducing activity on genomically unstable pluripotent stem cells, the synthetic peptide comprising a calreticulin expression inducing peptide sequence consisting of either of the following amino acid sequences:

```
                                       (SEQ ID NO: 1)
CRAKAGDPC;
and (SEQ ID NO: 2)
CEQKQEIRC.
```

12. The synthetic peptide according to claim 11, comprising a membrane-penetrating peptide sequence N-terminal or C-terminal to the calreticulin expression inducing peptide sequence.

13. The synthetic peptide according to claim 12, comprising the membrane-penetrating peptide sequence consisting of the following amino acid sequence:

```
                                       (SEQ ID NO: 5)
KKRTLRKNDRKKR.
```

14. The synthetic peptide according to claim 11, wherein the synthetic peptide has 30 or less amino acid residues in total.

15. The synthetic peptide according to claim 14, comprising any of the following amino acid sequences:

```
                                       (SEQ ID NO: 10)
KKRTLRKNDRKKRGGCRAKAGDPC;
and (SEQ ID NO: 11)
KKRTLRKNDRKKRGGCEQKQEIRC.
```

16. An agent comprising:
the synthetic peptide according to claim 11; and
at least one pharmaceutically acceptable carrier.

17. An artificially synthesised peptide exhibiting calreticulin expression inducing activity on genomically unstable pluripotent stem cells, the synthetic peptide having 30 or less amino acid residues in total and comprising any of the following amino acid sequences:

```
                                       (SEQ ID NO: 10)
KKRTLRKNDRKKRGGCRAKAGDPC;

(SEQ ID NO: 11)
KKRTLRKNDRKKRGGCEQKQEIRC;

(SEQ ID NO: 12)
KKRTLRKNDRKKRGGRAKAGDP;
and (SEQ ID NO: 13)
KKRTLRKNDRKKRGGEQKQEIR.
```

* * * * *

```
                         SEQUENCE LISTING

<160> NUMBER OF SEQ ID NOS: 13

<210> SEQ ID NO 1
<211> LENGTH: 9
<212> TYPE: PRT
<213> ORGANISM: Artificial sequence
<220> FEATURE:
<223> OTHER INFORMATION: Synthetic peptide

<400> SEQUENCE: 1

Cys Arg Ala Lys Ala Gly Asp Pro Cys
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic peptide

<400> SEQUENCE: 2

Cys Glu Gln Lys Gln Glu Ile Arg Cys
1               5

<210> SEQ ID NO 3
<211> LENGTH: 7
<212> TYPE: PRT
<213> ORGANISM: Artificial sequence
<220> FEATURE:
<223> OTHER INFORMATION: Synthetic peptide

<400> SEQUENCE: 3

Arg Ala Lys Ala Gly Asp Pro
1               5

<210> SEQ ID NO 4
<211> LENGTH: 7
<212> TYPE: PRT
<213> ORGANISM: Artificial sequence
<220> FEATURE:
<223> OTHER INFORMATION: Synthetic peptide

<400> SEQUENCE: 4

Glu Gln Lys Gln Glu Ile Arg
1               5

<210> SEQ ID NO 5
<211> LENGTH: 13
<212> TYPE: PRT
<213> ORGANISM: Artificial sequence
<220> FEATURE:
<223> OTHER INFORMATION: Synthetic peptide

<400> SEQUENCE: 5

Lys Lys Arg Thr Leu Arg Lys Asn Asp Arg Lys Lys Arg
1               5                   10

<210> SEQ ID NO 6
<211> LENGTH: 8
<212> TYPE: PRT
<213> ORGANISM: Artificial sequence
<220> FEATURE:
<223> OTHER INFORMATION: Synthetic peptide
```

```
<400> SEQUENCE: 6

Trp Arg Arg Gln Ala Arg Phe Lys
1               5

<210> SEQ ID NO 7
<211> LENGTH: 11
<212> TYPE: PRT
<213> ORGANISM: Artificial sequence
<220> FEATURE:
<223> OTHER INFORMATION: Synthetic peptide

<400> SEQUENCE: 7

Tyr Gly Arg Lys Lys Arg Arg Gln Arg Arg Arg
1               5                   10

<210> SEQ ID NO 8
<211> LENGTH: 11
<212> TYPE: PRT
<213> ORGANISM: Artificial sequence
<220> FEATURE:
<223> OTHER INFORMATION: Synthetic peptide

<400> SEQUENCE: 8

Tyr Ala Arg Ala Ala Ala Arg Gln Ala Arg Ala
1               5                   10

<210> SEQ ID NO 9
<211> LENGTH: 16
<212> TYPE: PRT
<213> ORGANISM: Artificial sequence
<220> FEATURE:
<223> OTHER INFORMATION: Artificial sequence

<400> SEQUENCE: 9

Arg Gln Ile Lys Ile Trp Phe Gln Asn Arg Arg Met Lys Trp Lys Lys
1               5                   10                  15

<210> SEQ ID NO 10
<211> LENGTH: 24
<212> TYPE: PRT
<213> ORGANISM: Artificial sequence
<220> FEATURE:
<223> OTHER INFORMATION: Synthetic peptide

<400> SEQUENCE: 10

Lys Lys Arg Thr Leu Arg Lys Asn Asp Arg Lys Arg Gly Gly Cys
1               5                   10                  15

Arg Ala Lys Ala Gly Asp Pro Cys
                20

<210> SEQ ID NO 11
<211> LENGTH: 24
<212> TYPE: PRT
<213> ORGANISM: Artificial sequence
<220> FEATURE:
<223> OTHER INFORMATION: Synthetic peptide

<400> SEQUENCE: 11

Lys Lys Arg Thr Leu Arg Lys Asn Asp Arg Lys Arg Gly Gly Cys
1               5                   10                  15

Glu Gln Lys Gln Glu Ile Arg Cys
                20

<210> SEQ ID NO 12
```

```
<211> LENGTH: 22
<212> TYPE: PRT
<213> ORGANISM: Artificial sequence
<220> FEATURE:
<223> OTHER INFORMATION: Synthetic peptide

<400> SEQUENCE: 12

Lys Lys Arg Thr Leu Arg Lys Asn Asp Arg Lys Lys Arg Gly Gly Arg
1               5                   10                  15

Ala Lys Ala Gly Asp Pro
            20

<210> SEQ ID NO 13
<211> LENGTH: 22
<212> TYPE: PRT
<213> ORGANISM: Artificial sequence
<220> FEATURE:
<223> OTHER INFORMATION: Synthetic peptide

<400> SEQUENCE: 13

Lys Lys Arg Thr Leu Arg Lys Asn Asp Arg Lys Lys Arg Gly Gly Glu
1               5                   10                  15

Gln Lys Gln Glu Ile Arg
            20
```